(12) United States Patent
Patient et al.

(10) Patent No.: US 9,580,415 B2
(45) Date of Patent: Feb. 28, 2017

(54) COMPOUNDS

(71) Applicant: Proximagen Limited, London (GB)

(72) Inventors: Lee Patient, Linton (GB); David Evans, Royston (GB); Iain Simpson, Cambridge (GB); Allison Powell, Longstanton (GB)

(73) Assignee: Proximagen Limited, Cambridge (GB)

( * ) Notice: Subject to any disclaimer, the term of this patent is extended or adjusted under 35 U.S.C. 154(b) by 0 days.

(21) Appl. No.: 14/774,749

(22) PCT Filed: Mar. 13, 2014

(86) PCT No.: PCT/GB2014/050764
§ 371 (c)(1),
(2) Date: Sep. 11, 2015

(87) PCT Pub. No.: WO2014/140591
PCT Pub. Date: Sep. 18, 2014

(65) Prior Publication Data
US 2016/0024080 A1 Jan. 28, 2016

(30) Foreign Application Priority Data
Mar. 13, 2013 (GB) .................... 1304527.3

(51) Int. Cl.
*C07D 401/02* (2006.01)
*C07D 401/10* (2006.01)
*C07D 471/04* (2006.01)

(52) U.S. Cl.
CPC .................. *C07D 471/04* (2013.01)

(58) Field of Classification Search
CPC ................ C07D 401/02; C07D 401/10; A61K 437/4353
USPC .......................... 546/121; 514/300
See application file for complete search history.

(56) References Cited

U.S. PATENT DOCUMENTS

| | | | |
|---|---|---|---|
| 7,405,300 B2 * | 7/2008 | Jiang .................... | A61K 31/404 544/373 |
| 9,428,498 B2 | 8/2016 | Espensen | |
| 2005/0054631 A1 | 3/2005 | Jiang et al. | |
| 2014/0275040 A1 | 9/2014 | Espensen et al. | |
| 2015/0258101 A1 | 9/2015 | Espensen et al. | |
| 2016/0046622 A1 | 2/2016 | Espensen et al. | |

FOREIGN PATENT DOCUMENTS

| | | |
|---|---|---|
| WO | 0238153 A1 | 5/2002 |
| WO | 03006003 A1 | 1/2003 |
| WO | 2005014530 A | 2/2005 |
| WO | 2007120528 A2 | 10/2007 |
| WO | 2010031789 A | 3/2010 |
| WO | 2010031791 A1 | 3/2010 |
| WO | 2010064020 A1 | 6/2010 |
| WO | 2010117935 A | 10/2010 |
| WO | 2011113798 A2 | 9/2011 |
| WO | 2013037411 A1 | 3/2013 |
| WO | 2013038189 A1 | 3/2013 |
| WO | 2013078254 A | 5/2013 |
| WO | 2014140592 A1 | 9/2014 |
| WO | 2015189534 A1 | 12/2015 |

OTHER PUBLICATIONS

CAS Registry No. 340159-15-1, Jun. 8, 2001, Compound 2-(2,3-dihydro-1,3-dimethyl-1H-benzimidazol-2-yl)-3-phenyl-3H-imidazo[4,5-c]pyridine.
Notice of Allowance mailed Jun. 24, 2015, in co-pending U.S. Appl. No. 14/208,056 (U.S. Publication No. 2014/0275040) filed Mar. 13, 2014.
International Search Report mailed Dec. 15, 2015 for PCT application No. PCT/GB2015/052690 filed Sep. 17, 2015.
International Search Report mailed on May 8, 2014 for PCT application No. PCT/GB2014/050765 filed on Mar. 13, 2014.
International Search Report mailed on Dec. 15, 2015 for PCT application No. PCT/GB2015/052691 filed Sep. 17, 2015.
UKIPO Search Report from Great Britain Patent Application 1304526.5 filed Mar. 13, 2013.
UKIPO Search Report mailed Jan. 13, 2016 for GB Application No. 1416444.6 filed on Sep. 17, 2014.
Database Registry [online], Chemical Abstracts Service, Columbus, Ohio, US; Jan. 19, 2011, XP002723294, database accession No. 1259952-23-2 abstract.
Dunkel, Petra et al. "Semicarbazide-sensitive amine oxidase/vascular adhesion protein-1: a patent survey," Expert Opin. Ther. Patents, 21(9): 1453-1471 (2011).
Melkonyan, Ferdinand S., et al. "One-pot synthesis of substituted indoles via titanium(iv) alkoxide mediated imine formation—copper-catalyzed N-arylation," RSC Advances, vol. 3, No. 22, Mar. 21, 2013, p. 8388, XP055113497.
PCT International Search Report dated Apr. 28, 2014 from PCT Application No. PCT/GB2014/050764 filed Mar. 13, 2014.
UKIPO Search Report dated Aug. 28, 2013 from application GB 1304527.3 filed Mar. 13, 2013.
Wilson, Robert J., et al. "Copper- and Palladium-Catalyzed Amidation Reactions for the Synthesis of Substituted Imidazo[4,5-c]pyridines," The Journal of Organic Chemistry, vol. 79, No. 5, Feb. 6, 2014, pp. 2203-2212, XP055113503.

(Continued)

*Primary Examiner* — Niloofar Rahmani
(74) *Attorney, Agent, or Firm* — Katharine A. Jackson Huebsch

(57) ABSTRACT

The compound of formula (I) are inhibitors of SSAO activity (Formula (I)) wherein the terms Y, Z, W, $R^1$ and $R^2$ are defined in the claims.

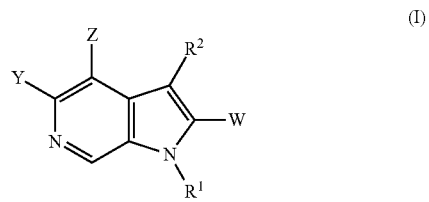

(I)

20 Claims, No Drawings

(56) References Cited

OTHER PUBLICATIONS

U.S. Appl. No. 14/208,056, filed Mar. 13, 2014, New Compounds.
U.S. Appl. No. 14/645,731, filed Mar. 12, 2015, New Compounds.
U.S. Appl. No. 14/775,046, filed Sep. 11, 2015, Imidazo[4,5-c]Pyridine and Pyrrolo[2,3-c]Pyridine Derivatives as SSAO Inhibitors.

* cited by examiner

COMPOUNDS

This application is a national stage application under 35 U.S.C. §371 of International Patent Application No. PCT/GB 2014/050764 filed Mar. 13, 2014 and published as International Publication No. WO2014/140591, which claims priority to Great Britain Patent Application No. 1304527.3 filed Mar. 13, 2013, each of which is incorporated by reference herein in its entirety.

FIELD OF THE INVENTION

The present invention relates to compounds which are inhibitors of SSAO activity. The invention also relates to pharmaceutical compositions comprising these compounds and to the use of these compounds in the treatment or prevention of medical conditions wherein inhibition of SSAO activity is beneficial, such as inflammatory diseases, immune disorders and the inhibition of tumour growth.

BACKGROUND ART

Semicarbazide-sensitive amine oxidase (SSAO) activity is an enzyme activity expressed by Vascular Adhesion Protein-1 (VAP-1) or Amine Oxidase, Copper Containing 3 (AOC3), and belongs to the copper-containing amine oxidase family of enzymes (EC.1.4.3.6). Therefore inhibitors of the SSAO enzyme may also modulate the biological functions of the VAP-1 protein. Members of this enzyme family are sensitive to inhibition by semicarbazide and utilize cupric ion and protein-derived topa quinone (TPQ) cofactor in the oxidative deamination of primary amines to aldehydes, hydrogen peroxide, and ammonia according to the following reaction:

$$R\text{—}CH_2\text{—}NH_2+O_2 \rightarrow R\text{—}CHO+H_2O_2+NH_3$$

Known substrates for human SSAO include endogenous methylamine and aminoacetone as well as some xenobiotic amines such as benzylamine [Lyles, *Int. J. Biochem. Cell Biol.* 1996, 28, 259-274; Klinman, *Biochim. Biophys. Acta* 2003, 1647 (1-2), 131-137; Matyus et al., *Curr. Med. Chem.* 2004, 11(10), 1285-1298; O'Sullivan et al., *Neurotoxicology* 2004, 25 (1-2), 303-315]. In analogy with other copper-containing amine oxidases, DNA-sequence analysis and structure determination suggest that the tissue-bound human SSAO is a homodimeric glycoprotein consisting of two 90-100 kDa subunits anchored to the plasma membrane by a single N-terminal membrane spanning domain [Morris et al., *J. Biol. Chem.* 1997, 272, 9388-9392; Smith et al., *J. Exp. Med.* 1998, 188, 17-27; Airenne et al., *Protein Science* 2005, 14, 1964-1974; Jakobsson et al., *Acta Crystallogr. D Biol. Crystallogr.* 2005, 61 (Pt 11), 1550-1562].

SSAO activity has been found in a variety of tissues including vascular and non-vascular smooth muscle tissue, endothelium, and adipose tissue [Lewinsohn, *Braz. J. Med. Biol. Res.* 1984, 17, 223-256; Nakos & Gossrau, *Folia Histochem. Cytobiol.* 1994, 32, 3-10; Yu et al., *Biochem. Pharmacol.* 1994, 47, 1055-1059; Castillo et al., *Neurochem. Int.* 1998, 33, 415-423; Lyles & Pino, *J. Neural. Transm. Suppl.* 1998, 52, 239-250; Jaakkola et al., *Am. J. Pathol.* 1999, 155, 1953-1965; Morin et al., *J. Pharmacol. Exp. Ther.* 2001, 297, 563-572; Salmi & Jalkanen, *Trends Immunol.* 2001, 22, 211-216]. In addition, SSAO protein is found in blood plasma and this soluble form appears to have similar properties as the tissue-bound form [Yu et al., *Biochem. Pharmacol.* 1994, 47, 1055-1059; Kurkijärvi et al., *J. Immunol.* 1998, 161, 1549-1557]. It has recently been shown that circulating human and rodent SSAO originates from the tissue-bound form [Göktürk et al., *Am. J. Pathol.* 2003, 163(5), 1921-1928; Abella et al., *Diabetologia* 2004, 47(3), 429-438; Stolen et al., *Circ. Res.* 2004, 95(1), 50-57], whereas in other mammals the plasma/serum SSAO is also encoded by a separate gene called AOC4 [Schwelberger, *J. Neural. Transm.* 2007, 114(6), 757-762].

The precise physiological role of this abundant enzyme has yet to be fully determined, but it appears that SSAO and its reaction products may have several functions in cell signalling and regulation. For example, recent findings suggest that SSAO plays a role in both GLUT4-mediated glucose uptake [Enrique-Tarancon et al., *J. Biol. Chem.* 1998, 273, 8025-8032; Morin et al., *J. Pharmacol. Exp. Ther.* 2001, 297, 563-572] and adipocyte differentiation [Fontana et al., *Biochem. J.* 2001, 356, 769-777; Mercier et al., *Biochem. J.* 2001, 358, 335-342]. In addition, SSAO has been shown to be involved in inflammatory processes where it acts as an adhesion protein for leukocytes [Salmi & Jalkanen, *Trends Immunol.* 2001, 22, 211-216; Salmi & Jalkanen, in "*Adhesion Molecules: Functions and Inhibition*" K. Ley (Ed.), 2007, pp. 237-251], and might also play a role in connective tissue matrix development and maintenance [Langford et al., *Cardiovasc. Toxicol.* 2002, 2(2), 141-150; Göktürk et al., *Am. J. Pathol.* 2003, 163(5), 1921-1928]. Moreover, a link between SSAO and angiogenesis has recently been discovered [Noda et al., *FASEB J.* 2008, 22(8), 2928-2935], and based on this link it is expected that inhibitors of SSAO have an anti-angiogenic effect.

WO2007146188 teaches that blocking SSAO activity inhibits leucocyte recruitment, reduces the inflammatory response, and is expected to be beneficial in prevention and treatment of seizures, for example, in epilepsy.

O'Rourke et al (J Neural Transm. 2007; 114(6):845-9) examined the potential of SSAO inhibitors in neurological diseases, having previously demonstrated the efficacy of SSAO inhibition in a rat model of stroke. An SSAO inhibitor is tested on relapsing-remitting experimental autoimmune encephalomyelitis (EAE), a mouse model that shares many characteristics with human multiple sclerosis. The data demonstrates the potential clinical benefit of small molecule anti-SSAO therapy in this model and therefore in treatment of human multiple sclerosis.

Several studies in humans have demonstrated that SSAO activity in blood plasma is elevated in conditions such as congestive heart failure, diabetes mellitus, Alzheimer's disease, and inflammation [Lewinsohn, *Braz. J. Med. Biol. Res.* 1984, 17, 223-256; Boomsma et al., *Cardiovasc. Res.* 1997, 33, 387-391; Ekblom, *Pharmacol. Res.* 1998, 37, 87-92; Kurkijärvi et al., *J. Immunol.* 1998, 161, 1549-1557; Boomsma et al., *Diabetologia* 1999, 42, 233-237; Meszaros et al., *Eur. J. Drug Metab. Pharmacokinet.* 1999, 24, 299-302; Yu et al., *Biochim. Biophys. Acta* 2003, 1647 (1-2), 193-199; Matyus et al., *Curr. Med. Chem.* 2004, 11(10), 1285-1298; O'Sullivan et al., *Neurotoxicology* 2004, 25 (1-2), 303-315; del Mar Hernandez et al., *Neurosci. Lett.* 2005, 384 (1-2), 183-187]. The mechanisms underlying these alterations of enzyme activity are not clear. It has been suggested that reactive aldehydes and hydrogen peroxide produced by endogenous amine oxidases contribute to the progression of cardiovascular diseases, diabetic complications and Alzheimer's disease [Callingham et al., *Prog. Brain Res.* 1995, 106, 305-321; Ekblom, *Pharmacol. Res.* 1998, 37, 87-92; Yu et al., *Biochim. Biophys. Acta* 2003, 1647 (1-2), 193-199; Jiang et al., *Neuropathol Appl Neurobiol.* 2008, 34(2), 194-204]. Furthermore, the enzymatic activity of SSAO is involved in the leukocyte extravasation process at sites of inflammation where SSAO has been shown to be strongly expressed on the vascular endothelium [Salmi et al., *Immunity* 2001, 14(3), 265-276; Salmi & Jalkanen, in "*Adhesion Molecules: Functions and Inhibition*" K. Ley (Ed.), 2007, pp. 237-251]. Accordingly, inhibition of SSAO has been suggested to have a therapeutic value in the prevention of diabetic complications and in inflammatory diseases [Ekblom, *Pharmacol. Res.* 1998, 37, 87-92; Salmi et al., *Immunity* 2001, 14(3), 265-276; Salter-Cid et al., *J. Pharmacol. Exp. Ther.* 2005, 315(2), 553-562].

SSAO knockout animals are phenotypically overtly normal but exhibit a marked decrease in the inflammatory responses evoked in response to various inflammatory stimuli [Stolen et al., *Immunity* 2005, 22(1), 105-115]. In addition, antagonism of its function in wild type animals in multiple animal models of human disease (e.g. carrageenan-induced paw inflammation, oxazolone-induced colitis, lipopolysaccharide-induced lung inflammation, collagen-induced arthritis, endotoxin-induced uveitis) by the use of antibodies and/or small molecules has been shown to be protective in decreasing the leukocyte infiltration, reducing the severity of the disease phenotype and reducing levels of inflammatory cytokines and chemokines [Kirton et al., *Eur. J. Immunol.* 2005, 35(11), 3119-3130; Salter-Cid et al., *J. Pharmacol. Exp. Ther.* 2005, 315(2), 553-562; McDonald et al., Annual Reports in Medicinal Chemistry 2007, 42, 229-243; Salmi & Jalkanen, in "*Adhesion Molecules: Functions and Inhibition*" K. Ley (Ed.), 2007, pp. 237-251; Noda et al., *FASEB J.* 2008 22(4), 1094-1103; Noda et al., *FASEB J.* 2008, 22(8), 2928-2935]. This anti-inflammatory protection seems to be afforded across a wide range of inflammatory models all with independent causative mechanisms, rather than being restricted to one particular disease or disease model. This would suggest that SSAO may be a key nodal point for the regulation of the inflammatory response, and it is therefore likely that SSAO inhibitors will be effective anti-inflammatory drugs in a wide range of human diseases. VAP-1 has also been implicated in the progression and maintenance of fibrotic diseases including those of the liver and lung. Weston and Adams (J Neural Transm. 2011, 118(7), 1055-64) have summarised the experimental data implicating VAP-1 in liver fibrosis, and Weston et al (EASL Poster 2010) reported that blockade of VAP-1 accelerated the resolution of carbon tetrachloride induced fibrosis. In addition VAP-1 has been implicated in inflammation of the lung (e.g. Singh et al., 2003, Virchows Arch 442:491-495) suggesting that VAP-1 blockers would reduce lung inflammation and thus be of benefit to the treatment of cystic fibrosis by treating both the pro-fibrotic and pro-inflammatory aspects of the disease.

SSAO (VAP-1) is up regulated in gastric cancer and has been identified in the tumour vasculature of human melanoma, hepatoma and head and neck tumours (Yoong K F, McNab G, Hubscher S G, Adams D H. (1998), J Immunol 160, 3978-88; Idala H, Salmi M, Alanen K, Gre'nman R, Jalkanen S (2001), Immunol. 166, 6937-6943; Forster-Horvath C, Dome B, Paku S, et al. (2004), Melanoma Res. 14, 135-40). One report (Marttila-Ichihara F, Castermans K, Auvinen K, Oude Egbrink M G, Jalkanen S, Griffioen A W, Salmi M. (2010), J Immunol. 184, 3164-3173.) has shown that mice bearing enzymically inactive VAP-1 grow melanomas more slowly, and have reduced tumour blood vessel number and diameter. The reduced growth of these tumours was also reflected in the reduced (by 60-70%) infiltration of myeloid suppressor cells. Encouragingly VAP-1 deficiency had no effect on vessel or lymph formation in normal tissue.

Small molecules of different structural classes have previously been disclosed as SSAO inhibitors, for example in WO 02/38153 (tetrahydroimidazo[4,5-c]pyridine derivatives), in WO 03/006003 (2-indanylhydrazine derivatives), in WO 2005/014530 (allylhydrazine and hydroxylamine (aminooxy) compounds) and in WO 2007/120528 (allylamino compounds). Additional SSAO inhibitors are disclosed in PCT/EP2009/062011 and PCT/EP2009/062018. Additional SSAO inhibitors are disclosed in PCT/GB2012/052265.

The invention described here relates to a new class of SSAO inhibitors with biological, pharmacological, and pharmacokinetic characteristics that make them suitable for use as prophylactic or therapeutic agents in a wide range of human inflammatory diseases and immune disorders. This therapeutic capacity is designed to block SSAO enzyme action, reducing the levels of pro-inflammatory enzyme products (aldehydes, hydrogen peroxide and ammonia) whilst also decreasing the adhesive capacity of immune cells and correspondingly their activation and final extra-vasation. Diseases where such an activity is expected to be therapeutically beneficial include all diseases where immune cells play a prominent role in the initiation, maintenance or resolution of the pathology, such as multiple sclerosis, arthritis and vasculitis.

DETAILED DESCRIPTION OF THE INVENTION

It has surprisingly been found that the compounds of formula (I) below are inhibitors of SSAO. They are therefore useful for the treatment or prevention of diseases in which inhibition of SSAO activity is beneficial, such as inflammation, inflammatory diseases, immune or autoimmune disorders, and inhibition of tumour growth.

According to the invention there is provided a compound of formula (I) or a pharmaceutically acceptable salt, or N-oxide thereof:

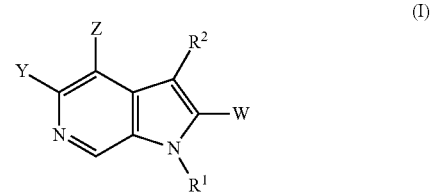

(I)

Wherein

Y is selected from hydrogen, hydroxyl, $-NH_2$, $-NH-C_{1-4}$-alkyl, $-NH$-halo-$C_{1-4}$-alkyl or $C_{1-4}$-alkoxy;

Z is selected from hydrogen, halogen, hydroxyl, cyano, $C_{1-4}$-alkyl, halo-$C_{1-4}$-alkyl, $C_{1-4}$-alkoxy halo-$C_{1-4}$-alkoxy, $CONH_2$, $SO_2NH_2$, $-NH_2$, $-NH-C_{1-4}$-alkyl, $-NH$-halo-$C_{1-4}$-alkyl;

$R^1$ is a phenyl ring, or a 5 or 6-membered heteroaryl ring, either ring being optionally substituted with one or more substituents selected from halogen, cyano, $C_{1-4}$-alkyl, halo-$C_{1-4}$-alkyl, cyano-$C_{1-4}$-alkyl, $C_{1-4}$-alkoxy, halo-$C_{1-4}$-alkoxy, $-NR^{4A}R^{4B}$, $-NR^6C(O)OR^5$, $-NR^6C(O)R^5$, $-NR^6C(O)NR^{4A}R^{4B}$, $-C(O)NR^{4A}R^{4B}$, $-C(O)R^5$, $-C(O)OR^5$, and $-NR^6S(O)_2R^5$;

W is a phenyl ring or a 5 or 6-membered heteroaryl ring, either ring being optionally substituted with one or more substituents selected from halogen, cyano, $C_{1-4}$-alkyl, halo-$C_{1-4}$-alkyl, cyano-$C_{1-4}$-alkyl, $C_{1-4}$-alkoxy, halo-$C_{1-4}$-alkoxy, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —SO$_2$R$^5$, —SO$_2$NR$^{4A}$R$^{4B}$ and —NR$^6$S(O)$_2$R$^5$;

R$^2$ is —B-Q-[R$^3$]$_n$ or —B—R$^3$;

wherein n=1, 2, 3, or 4

B is a bond, —O—, —NR$^5$—, —C(O)— or C$_{1-3}$-alkylene;

Q is a saturated or partially unsaturated 3-7 membered heterocyclic or C$_{3-7}$-cycloalkyl ring;

when R$^2$ is —B-Q-[R$^3$], R$^3$ is selected from hydrogen, halogen, cyano, amino, hydroxyl, oxo, C$_{1-4}$-alkyl, halo-C$_{1-4}$-alkyl, C$_{1-4}$-alkoxy, C$_{1-4}$alkoxy-C$_{1-4}$alkyl, hydroxy-C$_{1-4}$-alkyl, cyano-C$_{1-4}$-alkyl, amino-C$_{1-4}$-alkyl, C$_{1-4}$-alkylamino-C$_{1-4}$-alkyl, di(C$_{1-4}$-alkyl)amino-C$_{1-4}$-alkyl, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —NR$^6$S(O)$_2$R$^5$, —S(O)$_2$R$^5$, C$_{1-4}$-alkyl-NR$^6$C(O)OR$^5$, —C$_{1-4}$-alkyl-NR$^6$C(O)NR$^{4A}$R$^{4B}$, amino-C$_{1-4}$-alkoxy-C$_{1-4}$-alkyl-, (amino-C$_{1-4}$-alkyl)-amino-C$_{1-4}$-alkyl-, —C$_{1-4}$-alkyl-C(O)R$^5$, —OC(O)R$^5$, —C$_{1-4}$-alkyl-C(O)OR$^5$, —C$_{1-4}$-alkyl-C(O)NR$^{4A}$R$^{4B}$, —C$_{1-4}$-alkyl-NR$^6$C(O)NR$^{4A}$R$^{4B}$, 3-7 membered heterocyclyl, C$_{3-7}$-cycloalkyl, 3-7 membered heterocyclyl-C$_{1-4}$-alkyl-, (3-7 membered heterocyclyl-C$_{1-4}$-alkyl)-amino-C$_{1-4}$-alkyl-, phenyl-C$_{1-4}$-alkyl and 5 or 6-membered heteroaryl-C$_{1-4}$-alkyl, and wherein any phenyl or heteroaryl residue is optionally substituted with one or more substituents selected from halogen, cyano, C$_{1-4}$-alkyl, halo-C$_{1-4}$-alkyl, C$_{1-4}$-alkoxy, C$_{1-4}$alkoxy-C$_{1-4}$alkyl, hydroxy-C$_{1-4}$-alkyl, cyano-C$_{1-4}$-alkyl, amino-C$_{1-4}$-alkyl, C$_{1-4}$-alkylamino-C$_{1-4}$-alkyl, di(C$_{1-4}$-alkyl)amino-C$_{1-4}$-alkyl, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —NR$^6$S(O)$_2$R$^5$;

when R$^2$ is —B—R$^3$, R$^3$ is selected from —NH$_2$, C$_{1-4}$-alkoxy, C$_{1-4}$alkoxy-C$_{1-4}$alkyl, hydroxy-C$_{1-4}$-alkyl, cyano-C$_{1-4}$-alkyl, amino-C$_{1-4}$-alkyl, C$_{1-4}$-alkylamino-C$_{1-4}$-alkyl, di(C$_{1-4}$-alkyl)amino-C$_{1-4}$-alkyl, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A1}$R$^{4B}$, —C(O)R$^5$, —NR$^6$S(O)$_2$R$^5$, 3-7 membered heterocyclyl-C$_{1-4}$-alkyl-, phenyl-C$_{1-4}$-alkyl and heteroaryl-C$_{1-4}$-alkyl, and wherein any phenyl or heteroaryl residue is optionally substituted with one or more substituents selected from halogen, cyano, C$_{1-4}$-alkyl, halo-C$_{1-4}$-alkyl, C$_{1-4}$-alkoxy, C$_{1-4}$alkoxy-C$_{1-4}$ alkyl, hydroxy-C$_{1-4}$-alkyl, cyano-C$_{1-4}$-alkyl, amino-C$_{1-4}$-alkyl, C$_{1-4}$-alkylamino-C$_{1-4}$-alkyl, di(C$_{1-4}$-alkyl)amino-C$_{1-4}$-alkyl, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —NR$^6$S(O)$_2$R$^5$, provided that when R$^2$ is —B—R$^3$, and B is a bond and R$^3$ is —C(O)R$^5$, then R$^5$ is not hydrogen;

R$^{4A}$, R$^{4B}$ and R$^5$ are each independently selected from hydrogen, C$_{1-4}$-alkyl, hydroxy-C$_{1-4}$-alkyl, halo-C$_{1-4}$-alkyl, cyano-C$_{1-4}$-alkyl, amino-C$_{1-4}$-alkyl, C$_{1-4}$-alkylamino-C$_{1-4}$-alkyl, di(C$_{1-4}$-alkyl)amino-C$_{1-4}$-alkyl or C$_{1-4}$alkoxy-C$_{1-4}$alkyl, 3-7 membered heterocyclyl-, 3-7 membered heterocyclyl-C$_{1-4}$-alkyl-, C$_{1-4}$-alkyl-NR$^6$C(O)OR$^5$, C$_{1-4}$-alkyl-NR$^6$C(O)R$^5$, (3-7 membered heterocyclyl-C$_{1-4}$-alkyl)-amino-C$_{1-4}$-alkyl-, C$_{3-7}$-cycloalkyl, or 5 or 6-membered heteroaryl-C$_{1-4}$-alkyl wherein the alkyl part of the 5 or 6-membered heteroaryl-C$_{1-4}$-alkyl group is optionally substituted on one or more carbon atoms with group selected from halogen, C$_{1-4}$alkyl, or C$_{3-7}$-cycloalkyl, or one of the carbon atoms of the same alkyl part is substituted with two C$_{1-4}$alkyl substituents which together with the carbon atom to which they are attached form a spiro C$_{3-6}$-cycloalkyl ring, or R$^{4A}$ and R$^{4B}$ together with the nitrogen to which they are attached form a 4-7 membered cyclic amino group optionally substituted by one or more substituents selected from: oxo, halogen, hydroxyl, cyano, C$_{1-4}$-alkyl, halo-C$_{1-4}$-alkyl, C$_{1-4}$-alkoxy, C$_{1-4}$alkoxy-C$_{1-4}$alkyl-, halo-C$_{1-4}$-alkoxy, —C(O)NR$^{4A}$R$^{4B}$, —CONH$_2$, —SO$_2$NH$_2$, —NH$_2$, —NHC$_{1-4}$-alkyl, —NHhalo-C$_{1-4}$-alkyl, —C(O)R$^5$, —C(O)OR$^5$ or —SO$_2$R$^5$, or C$_{3-7}$-cycloalkyl;

unless otherwise specified the 3-7 membered heterocyclyl, or the heterocyclyl part of the 3-7 membered heterocyclyl-C$_{1-4}$-alkyl-, (3-7 membered heterocyclyl-C$_{1-4}$-alkyl)-amino-C$_{1-4}$-alkyl-, or (3-7 membered heterocyclyl-C$_{1-4}$-alkyl)-C(O)— group is optionally substituted with one or more substituents selected from C$_{1-4}$-alkyl-, —C(O)OR$^5$, —C(O)R$^5$, —C(O)NR$^{4A}$R$^{4B}$, —NR$^{4A}$R$^{4B}$, —C$_{1-4}$-alkyl-C(O)NR$^{4A}$R$^{4B}$, or C$_{1-4}$alkoxy-C$_{1-4}$alkyl; and R$^{4A1}$ is selected from C$_{1-4}$-alkyl, hydroxy-C$_{1-4}$-alkyl, halo-C$_{1-4}$-alkyl, cyano-C$_{1-4}$-alkyl, amino-C$_{1-4}$-alkyl, C$_{1-4}$-alkylamino-C$_{1-4}$-alkyl, di(C$_{1-4}$-alkyl)amino-C$_{1-4}$-alkyl or C$_{1-4}$alkoxy-C$_{1-4}$alkyl; or R$^{4A1}$ and R$^{4B}$ together with the nitrogen to which they are attached form a 4-7 membered cyclic amino group optionally substituted by one or more substituents selected from: oxo, halogen, hydroxyl, cyano, C$_{1-4}$-alkyl, halo-C$_{1-4}$-alkyl, C$_{1-4}$-alkoxy, C$_{1-4}$alkoxy-C$_{1-4}$alkyl-, halo-C$_{1-4}$-alkoxy, —CONH$_2$, —SO$_2$NH$_2$, —NH$_2$, —NHC$_{1-4}$-alkyl, —NHhalo-C$_{1-4}$-alkyl, —C(O)R$^5$, —C(O)OR$^5$ or —SO$_2$R$^5$, or C$_{3-7}$-cycloalkyl.

In addition to the surprising activity of the compounds of formula (I) at the SSAO receptor, it has been surprisingly found that the claimed compounds have surprisingly low activity at the hERG ion channel. The person skilled in the art, for example a medicinal chemist, understands that low hERG activity is an important property for a pharmaceutical drug compound. Without wishing to be bound by theory, it is believed that the —W group as defined in claim 1 is especially advantageous in relation to reduced hERG activity.

It is expected that compounds of the invention may be prepared in the form of hydrates, and solvates. Any reference herein, including the claims herein, to "compounds with which the invention is concerned" or "compounds of the invention" or "the present compounds", and the like, includes reference to salts, hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in an amorphous form and/or several polymorphic forms and may be obtained in different crystal habits. Any reference herein, including the claims herein, to "compounds with which the invention is concerned" or "compounds of the invention" or "the present compounds", and the like, includes reference to the compounds irrespective of amorphous or polymorphic form.

Since compounds of the invention have a nitrogen atom in an aromatic ring they may form N-oxides, and the invention includes compounds of the invention in their N-oxide form.

DEFINITIONS

The following definitions shall apply throughout the specification and the appended claims, unless otherwise stated or indicated.

The term "C$_{1-4}$-alkyl" denotes a straight or branched alkyl group having from 1 to 4 carbon atoms. For parts of the range C$_{1-4}$-alkyl all subgroups thereof are contemplated such as C$_{1-3}$-alkyl, C$_{1-2}$-alkyl, C$_{2-4}$-alkyl, C$_{2-3}$-alkyl and $C_{3-4}$-alkyl. Examples of said $C_{1-4}$-alkyl include methyl, ethyl, n-propyl, isopropyl, n-butyl, isobutyl, sec-butyl and tert-butyl.

Unless otherwise specified, the term "$C_{3-7}$-cycloalkyl" refers to a monocyclic saturated or partially unsaturated hydrocarbon ring system having from 3 to 7 carbon atoms. Examples of said $C_{3-7}$-cycloalkyl include cyclopropyl, cyclobutyl, cyclopentyl, cyclohexyl, cyclohexenyl, cycloheptyl, and cycloheptenyl. For parts of the range "$C_{3-7}$-cycloalkyl" all subgroups thereof are contemplated such as $C_{3-7}$-cycloalkyl, $C_{3-6}$-cycloalkyl, $C_{3-5}$-cycloalkyl, $C_{3-4}$-cycloalkyl, $C_{4-7}$-cycloalkyl, $C_{4-6}$-cycloalkyl, $C_{4-5}$-cycloalkyl, $C_{5-7}$-cycloalkyl, $C_{5-6}$-cycloalkyl, and $C_{6-7}$-cycloalkyl.

The term "$C_{1-4}$-alkoxy" refers to a straight or branched $C_{1-4}$-alkyl group which is attached to the remainder of the molecule through an oxygen atom. For parts of the range $C_{1-4}$-alkoxy, all subgroups thereof are contemplated such as $C_{1-3}$-alkoxy, $C_{1-2}$-alkoxy, $C_{2-4}$-alkoxy, $C_{2-3}$-alkoxy and $C_{3-4}$-alkoxy. Examples of said $C_{1-4}$-alkoxy include methoxy, ethoxy, n-propoxy, isopropoxy, n-butoxy, isobutoxy, sec-butoxy and tert-butoxy.

The term "halo$C_{1-4}$-alkoxy" refers to a straight or branched $C_{1-4}$-alkyl group which is attached to the remainder of the molecule through an oxygen atom and has one or more hydrogen atoms thereof replaced with halogen such as fluoro or chloro. For parts of the range $C_{1-4}$-alkoxy, all subgroups thereof are contemplated. Examples of said $C_{1-4}$-alkoxy include trifluoromethoxy.

The term "hydroxy-$C_{1-4}$-alkyl" denotes a straight or branched $C_{1-4}$-alkyl group that has one or more hydrogen atoms thereof replaced with OH. Examples of said hydroxy-$C_{1-4}$-alkyl include hydroxymethyl, 2-hydroxyethyl and 2,3-dihydroxypropyl.

The term "halo-$C_{1-4}$-alkyl" denotes a straight or branched $C_{1-4}$-alkyl group that has one or more hydrogen atoms thereof replaced with halogen. Examples of said halo-$C_{1-4}$-alkyl include fluoromethyl, trifluoromethyl, trichloromethyl and 2-fluoroethyl.

The term "cyano-$C_{1-4}$-alkyl" denotes a straight or branched $C_{1-4}$-alkyl group that has one or more hydrogen atoms thereof replaced with cyano. Examples of said cyano-$C_{1-4}$-alkyl include cyanomethyl, 2-cyanoethyl and 3-cyanopropyl.

The term "amino-$C_{1-4}$-alkyl" denotes a straight or branched $C_{1-4}$-alkyl group substituted with an amino group. Examples of said amino-$C_{1-4}$-alkyl group include aminomethyl and 2-aminoethyl.

The term "$C_{1-4}$-alkylamino-$C_{1-4}$-alkyl" denotes an amino-$C_{1-4}$-alkyl group as defined above, wherein the amino group is substituted with a straight or branched $C_{1-4}$-alkyl group. Examples of said $C_{1-4}$-alkylamino-$C_{1-4}$-alkyl include methylaminoethyl and ethylaminopropyl.

The term "di($C_{1-4}$-alkyl)amino-$C_{1-4}$-alkyl" denotes an amino-$C_{1-4}$-alkyl group as defined above, wherein the amino group is disubstituted with straight or branched $C_{1-4}$-alkyl groups, which can be the same or different. Examples of said di($C_{1-4}$-alkyl)amino-$C_{1-4}$-alkyl include N,N-dimethylaminomethyl, N-ethyl-N-methylaminoethyl and N,N-diethylaminomethyl.

The terms "heteroaryl" and "heteroaromatic ring" denote a monocyclic heteroaromatic ring comprising 5 to 6 ring atoms in which one or more of the ring atoms are other than carbon, such as nitrogen, sulphur or oxygen. Examples of heteroaryl groups include furyl, pyrrolyl, thienyl, oxazolyl, isoxazolyl, imidazolyl, thiazolyl, isothiazolyl, pyridinyl, pyrimidinyl, tetrazolyl, pyrazolyl, pyridazinyl, pyrazinyl and thiadiazolyl.

The terms "heterocyclyl" and "heterocyclic ring" denote a non-aromatic, fully saturated or partially unsaturated, preferably fully saturated, monocyclic ring system having from 3 to 7 ring atoms, especially 5 or 6 ring atoms, in which one or more of the ring atoms are other than carbon, such as nitrogen, sulphur or oxygen. Examples of heterocyclic groups include piperidinyl, homopiperidinyl, morpholinyl, homomorpholinyl, azepanyl, piperazinyl, homopiperazinyl, oxo-piperazinyl, diazepinyl, tetrahydropyranyl, pyrrolidinyl, tetrahydrofuranyl, and dihydropyrrolyl, groups.

The term "heterocyclic-$C_{1-3}$-alkyl" refers to a heterocyclic ring that is directly linked to a straight or branched $C_{1-3}$-alkyl group via a carbon or nitrogen atom of said ring. Examples of said heterocyclic-$C_{1-4}$-alkyl include piperidin-4-ylmethyl, piperidin-1-ylmethyl, morpholin-4-yl-methyl and piperazin-4-ylmethyl. The $C_{1-3}$-alkyl part, which includes methylene, ethylene, propylene or butylene, is optionally substituted by one or more substituents selected from halogen, amino, methoxy, or hydroxyl.

The term "$C_{1-3}$-alkylene" denotes a straight or branched divalent saturated hydrocarbon chain having from 1 to 3 carbon atoms. The $C_{1-3}$-alkylene chain may be attached to the rest of the molecule and to the radical group through one carbon within the chain or through any two carbons within the chain. Examples of $C_{1-3}$-alkylene radicals include methylene [—$CH_2$—], 1,2-ethylene [—$CH_2$—$CH_2$—], 1,1-ethylene [—CH($CH_3$)—], 1,2-propylene [—$CH_2$—CH($CH_3$)—] and 1,3-propylene [—$CH_2$—$CH_2$—$CH_2$—]. When referring to a "$C_{1-3}$-alkylene" radical, all subgroups thereof are contemplated, such as $C_{1-2}$-alkylene, $C_{2-3}$-alkylene.

"Halogen" refers to fluorine, chlorine, bromine or iodine, preferably fluorine and chlorine, most preferably fluorine.

"Hydroxy" refers to the —OH radical.

"Cyano" refers to the —CN radical.

"Oxo" refers to the carbonyl group =O.

"Optional" or "optionally" means that the subsequently described event or circumstance may but need not occur, and that the description includes instances where the event or circumstance occurs and instances in which it does not.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

"Prodrugs" refers to compounds that may be converted under physiological conditions or by solvolysis to a biologically active compound of the invention. A prodrug may be inactive when administered to a subject in need thereof, but is converted in vivo to an active compound of the invention. Prodrugs are typically rapidly transformed in vivo to yield the parent compound of the invention, e.g. by hydrolysis in the blood. The prodrug compound usually offers advantages of solubility, tissue compatibility or delayed release in a mammalian organism (see Silverman, R. B., *The Organic Chemistry of Drug Design and Drug Action*, $2^{nd}$ Ed., Elsevier Academic Press (2004), pp. 498-549). Prodrugs of a compound of the invention may be prepared by modifying functional groups, such as a hydroxy, amino or mercapto groups, present in a compound of the invention in such a way that the modifications are cleaved, either in routine manipulation or in vivo, to the parent compound of the invention. Examples of prodrugs include, but are not limited to, acetate, formate and succinate derivatives of hydroxy functional groups or phenyl carbamate derivatives of amino functional groups.

Throughout the specification and the appended claims, a given chemical formula or name shall also encompass all salts, hydrates, solvates, N-oxides and prodrug forms thereof. Further, a given chemical formula or name shall encompass all tautomeric and stereoisomeric forms thereof. Tautomers include enol and keto forms. Stereoisomers include enantiomers and diastereomers. Enantiomers can be present in their pure forms, or as racemic (equal) or unequal mixtures of two enantiomers. Diastereomers can be present in their pure forms, or as mixtures of diastereomers. Diastereomers also include geometrical isomers, which can be present in their pure cis or trans forms or as mixtures of those.

The compounds of formula (I) may be used as such or, where appropriate, as pharmacologically acceptable salts (acid or base addition salts) thereof. The pharmacologically acceptable addition salts mentioned below are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

The Group Y

In an embodiment Y is selected from hydrogen, hydroxyl, —NH$_2$, —NH—C$_{1-4}$-alkyl such as NH-Methyl, —NH-ethyl, or NH-isopropyl, —NH-halo-C$_{1-4}$-alkyl such as —NHtrifluoromethyl, or —C$_{1-4}$-alkoxy such as methoxy. In an embodiment Y is hydrogen.

The Group Z

In an embodiment Z is selected from hydrogen, halogen such as fluoro or chloro, hydroxyl, cyano, C$_{1-4}$-alkyl such as methyl or isopropyl, halo-C$_{1-4}$-alkyl such as triflouromethyl, C$_{1-4}$-alkoxy such as methoxy, halo-C$_{1-4}$-alkoxy such as trifluoromethoxy, —CONH$_2$, —SO$_2$NH$_2$, —NH$_2$, —NHC$_{1-4}$-alkyl such as NH-Methyl, —NH— ethyl, or NH-isopropyl, or —NHhalo-C$_{1-4}$-alkyl. In an embodiment Z is hydrogen.

The Group R$^1$

In an embodiment R$^1$ is a phenyl ring, or a 5 or 6-membered heteroaryl ring either ring being optionally substituted with one or more substituents selected from halogen such as fluoro or chloro, cyano, C$_{1-4}$-alkyl such as methyl or isopropyl, halo-C$_{1-4}$-alkyl such as trifluoromethyl, cyano-C$_{1-4}$-alkyl such as methylcyano, C$_{1-4}$-alkoxy such as methoxy, or haloC$_{1-4}$-alkoxy such as trifluoromethoxy, —NR$^{4A}$R$^{4B}$ such as NH$_2$, —NHMethyl, —NHisopropyl, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$ such as COCH$_3$, —C(O)OR$^5$, and —NR$^6$S(O)$_2$R$^5$. In an embodiment R$^1$ is phenyl, pyridyl, pyrrolyl, furanyl, imidazolyl, or thiophenyl optionally substituted as defined in formula (I).

The Group W

In an embodiment W is a phenyl ring. In an alternative embodiment W a heteroaryl ring selected from pyridyl, pyridazinyl, pyrazinyl, pyrimidinyl, imidazolyl, tetrazolyl, oxazolyl, thiazolyl, 1,2,3-triazolyl, or 1,2,4-triazolyl. Any of the aforementioned rings are optionally substituted with one or more substituents as defined in relation to formula (I).

In an embodiment W is selected from any one of the following rings, any of which rings is optionally substituted with one or more substituents as defined in formula (I).

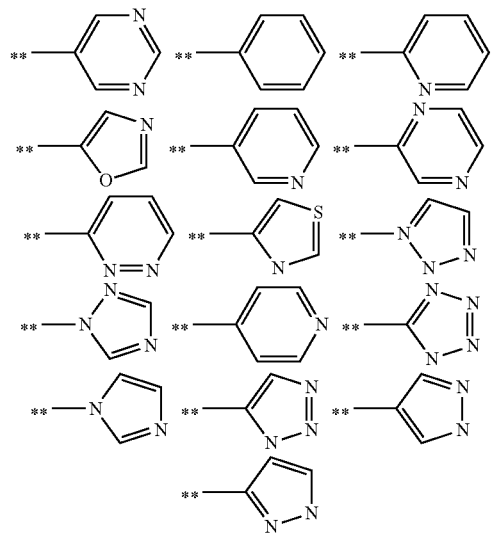

wherein bond marked ** is directly connected to the rest of the molecule. In an embodiment W is imidazolyl and the imidazolyl ring is connected to the pyrrolopyridine core (i.e. the rest of the molecule) via an imidazoly ring carbon atom. In an embodiment W is substituted with one or more groups selected from fluoro, chloro, cyano, methyl, methoxy, trifluoromethyl, trifluoromethoxy or a 3-7 heteroaryl group such as azetidine, pyrrolidine, piperidine, piperazine, homopiperidine, homopiperazine, morpholine, tetrahydrofuran, or tetrahydropyran.

The Group R$^2$

R$^2$ is —B-Q-[R$^3$]$_n$ or —B—R$^3$. In an embodiment R$^2$ is Q-[R$^3$]$_n$. In an embodiment R$^2$ is —B—R$^3$, B is —C$_{1-3}$-alkylene-, and —R$^3$ is —NR$^{4A}$R$^{4B}$; in a embodiment R$^{4A}$ and R$^{4B}$ are each independently selected from hydrogen and C$_{1-4}$-alkyl such as methyl, ethyl, propyl or isopropyl.

n is 1, 2, 3, or 4. In an embodiment n is 0. In an embodiment n is 1 or 2.

The Group B

B is selected from the group consisting of a direct bond, —O—, —NR$^5$ such as —NH— or —N(CH$_3$)—, —C(O)— or C$_{1-3}$-alkylene such as methylene, ethylene or propylene. In an embodiment B is a direct bond. In an alternative embodiment B is methylene optionally substituted with fluoro, or methyl.

The Group Q

Q is a saturated or partially unsaturated 3-7 membered heterocyclic or $C_{3-7}$-cycloalkyl ring. In an embodiment Q is selected from the following rings: Azetidinyl, pyrrolidinyl, piperidinyl, piperazinyl, homopiperidinyl, homopiperazinyl, morpholinyl, homomorpholinyl, tetrahydrofuranyl, tetrahydropyranyl, cyclopropyl, cyclobutyl, cyclopentyl or cyclohexyl.

In an embodiment Q is selected from piperidinyl, morpholinyl, or piperazinyl.

The Group $R^3$

The definition of $R^3$ differs depending on whether $R^2$ is —B-Q-[$R^3$]$_n$ or —B—$R^3$. The definition of $R^3$ in each case is set out above in relation to formula (I).

In an embodiment $R^3$ is —C(O)NR$^{4A}$R$^{4B}$.

In an embodiment the groups Q and $R^3$ together form the following $R^2$ group:

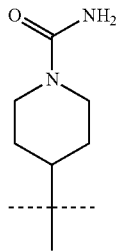

$R^{4A}$, $R^{4B}$ and $R^5$ are each independently selected from hydrogen, $C_{1-4}$-alkyl such as methyl, ethyl or isopropyl, hydroxy-$C_{1-4}$-alkyl, halo-$C_{1-4}$-alkyl such as trifluoromethyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl or $C_{1-4}$alkoxy-$C_{1-4}$alkyl, 3-7 membered heterocyclyl-, 3-7 membered heterocyclyl-$C_{1-4}$-alkyl-, $C_{1-4}$-alkyl-NR$^6$C(O)OR$^5$, $C_{1-4}$-alkyl-NR$^6$C(O)R$^5$, (3-7 membered heterocyclyl-$C_{1-4}$-alkyl)-amino-$C_{1-4}$-alkyl-, $C_{3-7}$-cycloalkyl, or 5 or 6-membered heteroaryl-$C_{1-4}$-alkyl wherein the alkyl part of the 5 or 6-membered heteroaryl-$C_{1-4}$-alkyl group is optionally substituted on one or more carbon atoms with group selected from halogen, $C_{1-4}$alkyl, or $C_{3-7}$-cycloalkyl, or one of the carbon atoms of the same alkyl part is substituted with two $C_{1-4}$alkyl substituents which together with the carbon atom to which they are attached form a spiro $C_{3-6}$-cycloalkyl ring, or $R^{4A}$ and $R^{4B}$ together with the nitrogen to which they are attached form a 4-7 membered cyclic amino group such as azetidine, pyrrolidine, piperidine, piperazine, homopiperidine, homopiperazine, morpholine, or homomorpholine, any of which rings are optionally substituted by one or more substituents selected from: oxo, halogen such as fluoro or chloro, hydroxyl, cyano, $C_{1-4}$-alkyl such as methyl, ethyl, n-propyl or isopropyl, halo-$C_{1-4}$-alkyl such as trifluoromethyl, $C_{1-4}$-alkoxy such as methoxy, $C_{1-4}$alkoxy-$C_{1-4}$alkyl-, halo-$C_{1-4}$-alkoxy such as trifluoromethoxy, —C(O)NR$^{4A}$R$^{4B}$, —CONH$_2$, —SO$_2$NH$_2$, —NH$_2$, —NHC$_{1-4}$-alkyl, —NHhalo-$C_{1-4}$-alkyl, —C(O)R$^5$ such as —C(O)CH$_3$, —C(O)OR$^5$ or —SO$_2$R$^5$, or $C_{3-7}$-cycloalkyl such as cyclopropyl;

unless otherwise specified 3-7 membered heterocyclyl, or the heterocyclyl part of the 3-7 membered heterocyclyl-$C_{1-4}$-alkyl-, (3-7 membered heterocyclyl-$C_{1-4}$-alkyl)-amino-$C_{1-4}$-alkyl-, or (3-7 membered heterocyclyl-$C_{1-4}$-alkyl)-C(O)— group is optionally substituted with one or more substituents selected from $C_{1-4}$-alkyl-, —C(O)OR$^5$, —C(O) R$^5$, —C(O)NR$^{4A}$R$^{4B}$, —NR$^{4A}$R$^{4B}$, —C$_{1-4}$-alkyl-C(O) NR$^{4A}$R$^{4B}$, or $C_{1-4}$alkoxy-$C_{1-4}$alkyl; and $R^{4A1}$ is selected from $C_{1-4}$-alkyl, hydroxy-$C_{1-4}$-alkyl, halo-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl or $C_{1-4}$alkoxy-$C_{1-4}$alkyl; or $R^{4A1}$ and $R^{4B}$ together with the nitrogen to which they are attached form a 4-7 membered cyclic amino group optionally substituted by one or more substituents selected from: oxo, halogen, hydroxyl, cyano, $C_{1-4}$-alkyl, halo-$C_{1-4}$-alkyl, $C_{1-4}$-alkoxy, $C_{1-4}$alkoxy-$C_{1-4}$alkyl-, halo-$C_{1-4}$-alkoxy, —CONH$_2$, —SO$_2$NH$_2$, —NH$_2$, —NHC$_{1-4}$-alkyl, —NHhalo-$C_{1-4}$-alkyl, —C(O)R$^5$, —C(O)OR$^5$ or —SO$_2$R$^5$, or $C_{3-7}$-cycloalkyl.

$R^6$ is hydrogen or $C_{1-4}$-alkyl. In an embodiment $R^6$ is hydrogen of methyl.

In an embodiment $R^5$ is hydrogen or methyl.

Further $R^2$ Groups

Patent application number PCT/EP2011/053818 (published as WO2011/113798) discloses compounds having SSAO inhibitory activity. Related compounds also having SSAO inhibitory activity are in disclosed in PCT applications PCT/EP2011/065967 (published as WO2013/037411) and PCT/GB2012/052265 (published as WO2013/038189). Compounds disclosed in these three applications are structurally related to the claimed compounds. By virtue of their related structures it is expected that the compounds disclosed in the above three patent applications will have the same binding mode as the compounds of the present invention. It is therefore credible that the structure activity relationship (SAR) of the compounds disclosed in the above applications is transferrable to the claimed compounds.

Thus transfer of the $R^2$ groups from the specific Examples of the above three patent applications to the claimed compounds of formula (I) is expected to result in compounds of formula (I) compounds having SSAO inhibitory activity. In other words, the scope of the present claims is supported by the specific Examples of the above three patent applications.

Thus the present invention makes available a class of SSAO inhibitor compounds of formula (I) wherein $R^2$ is selected from the following list of "further $R^2$ groups":

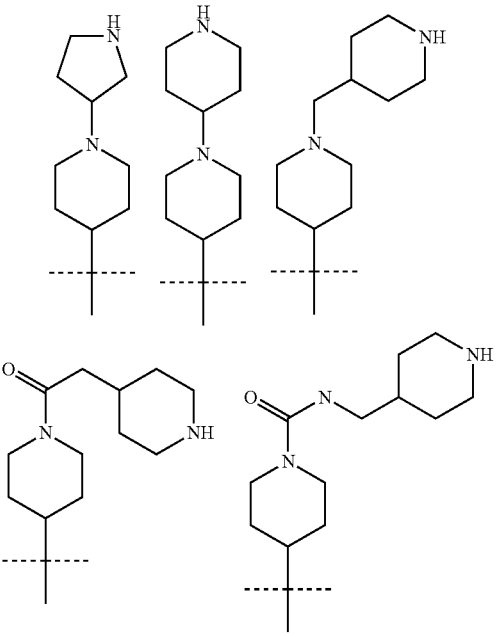

-continued
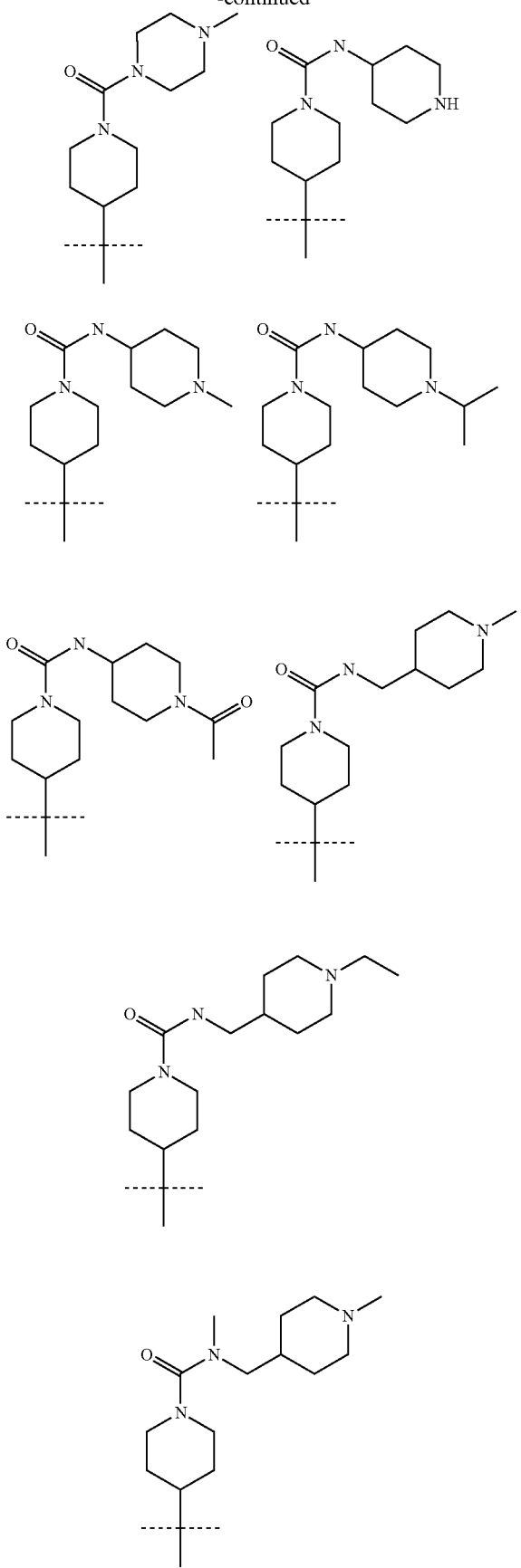
-continued
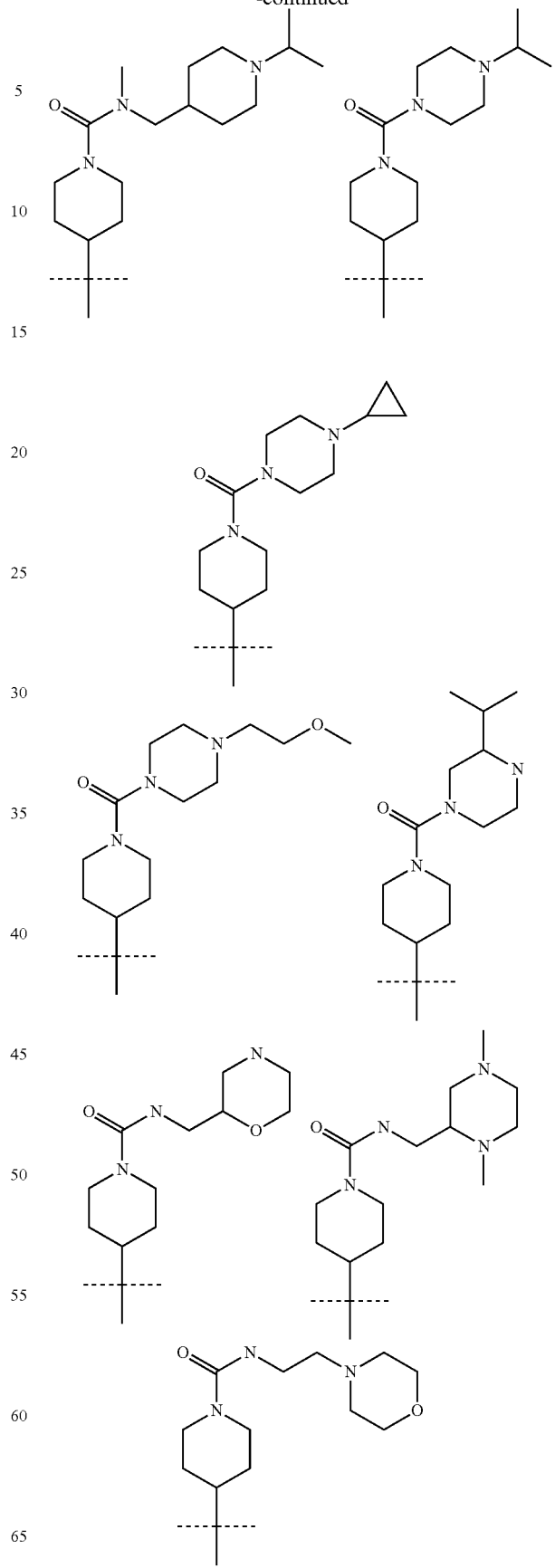

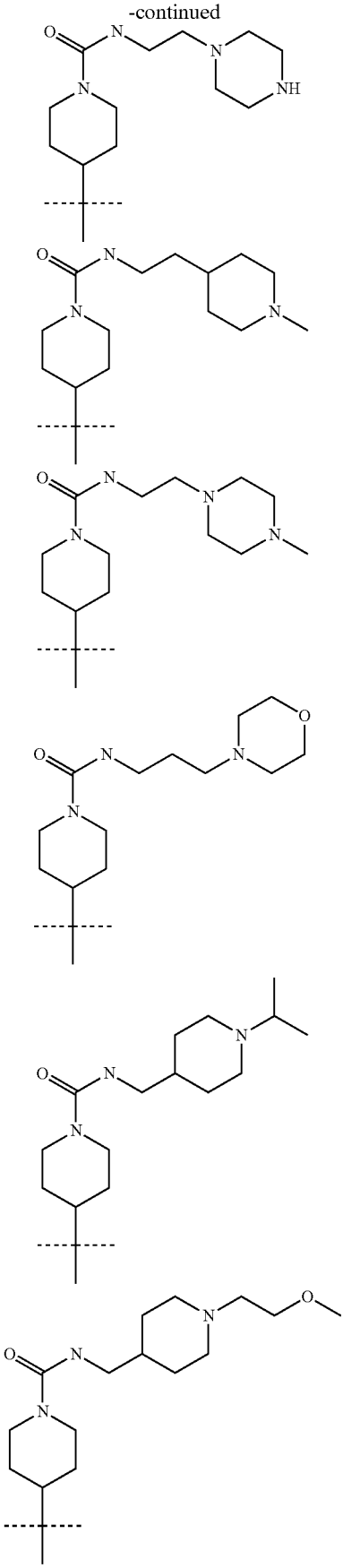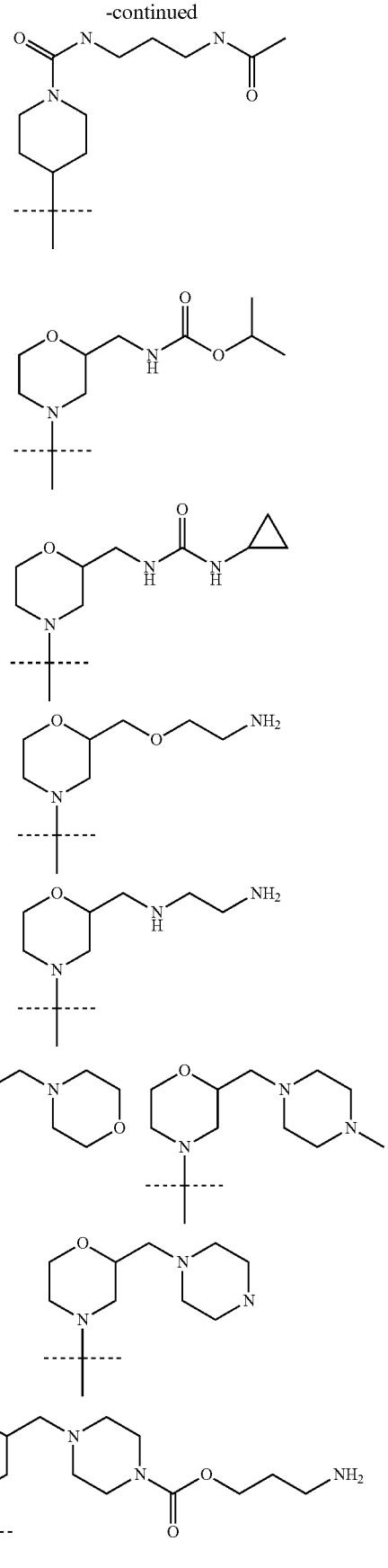

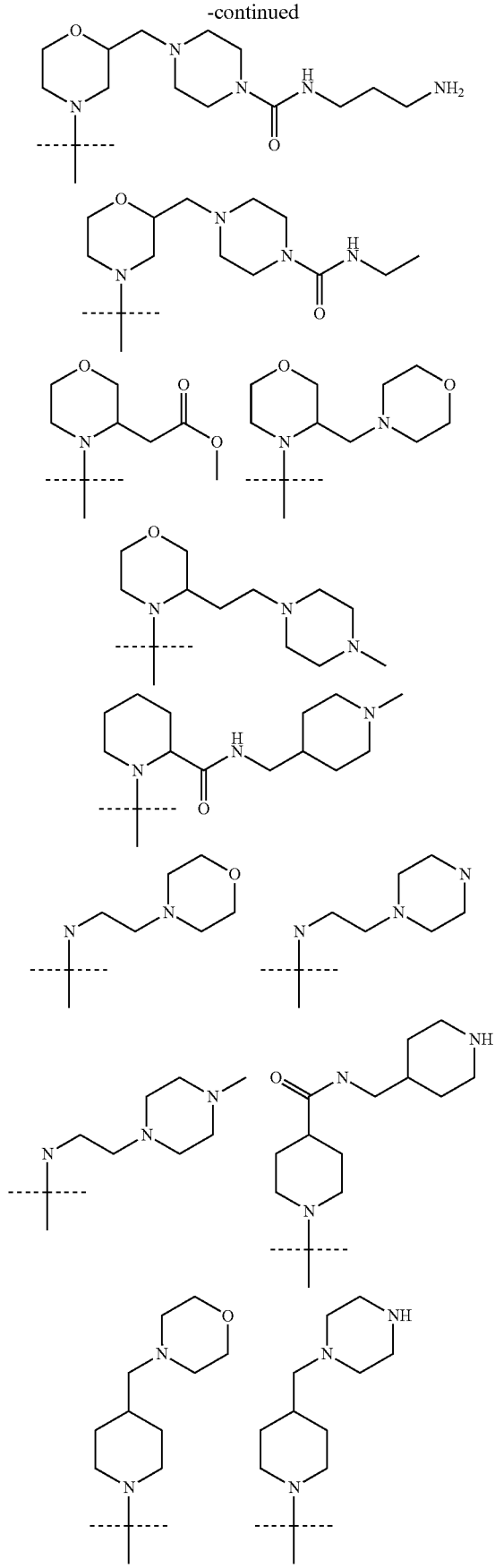
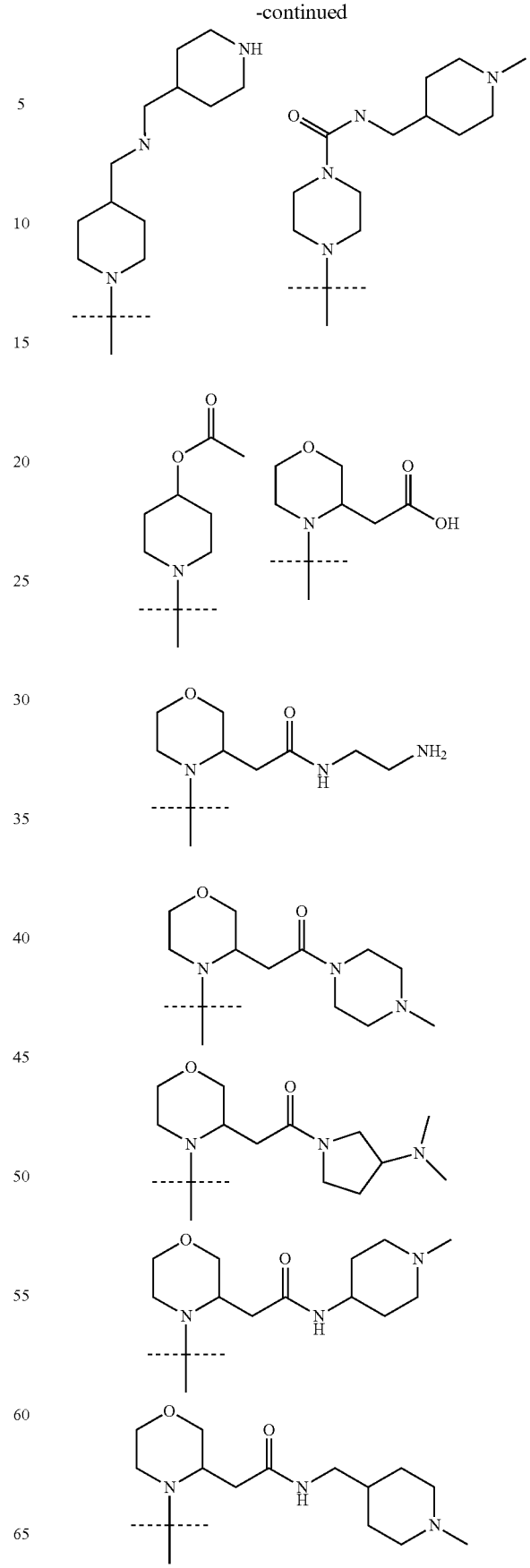

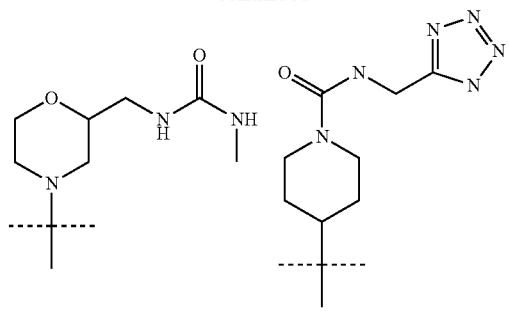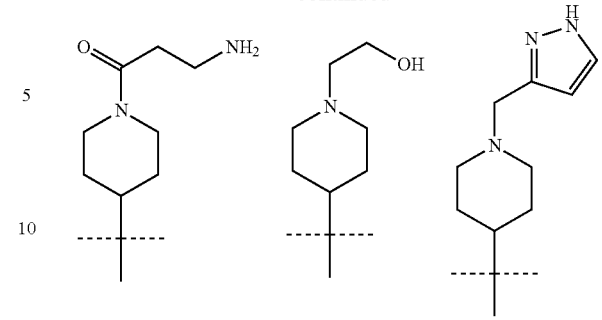
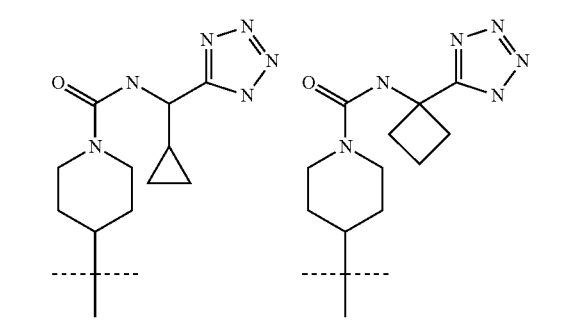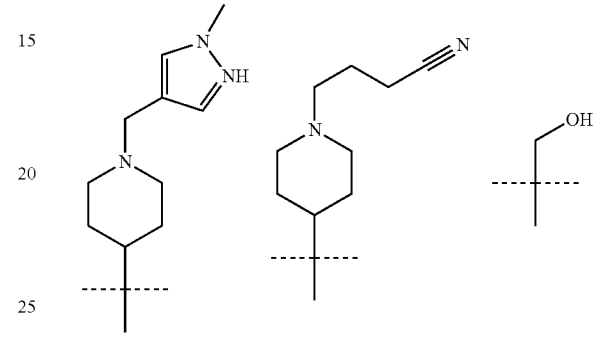
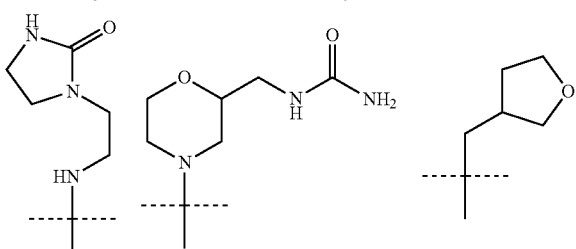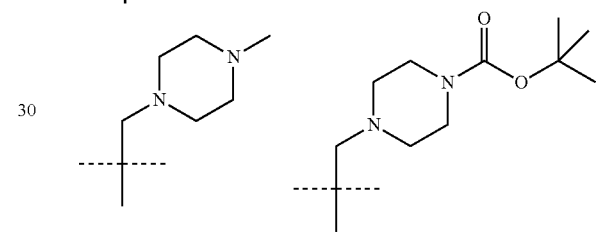
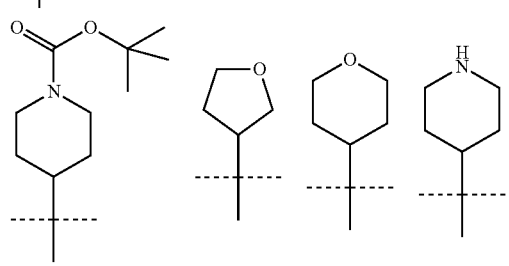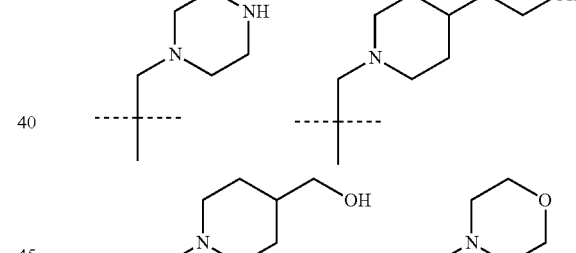
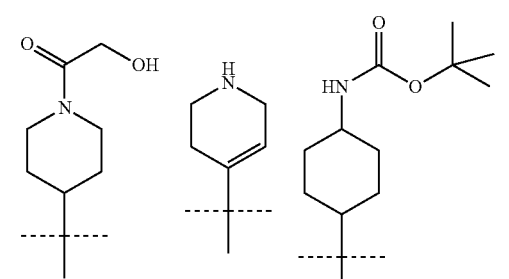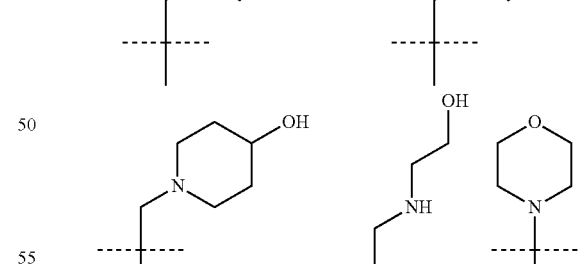
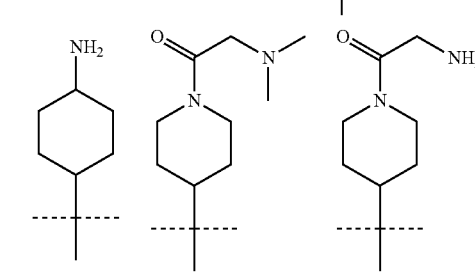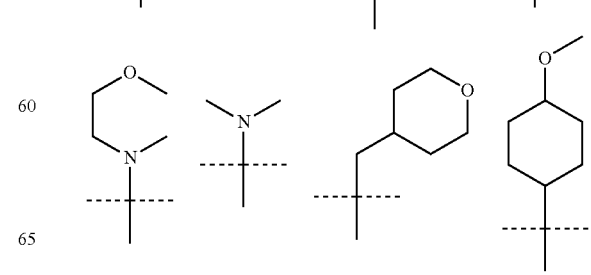

-continued
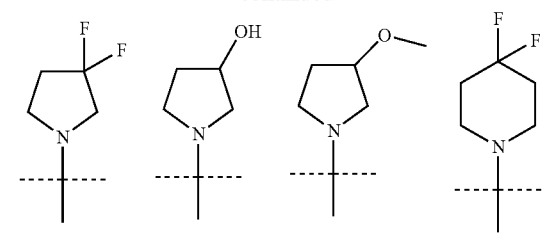
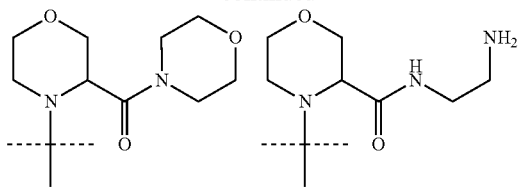
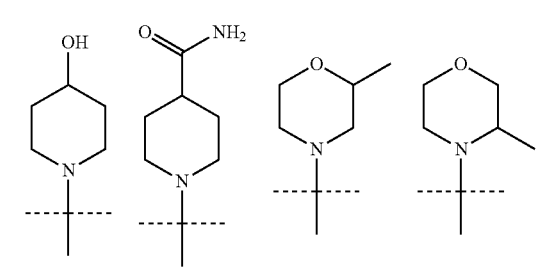
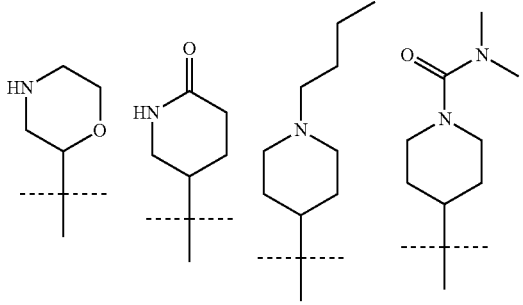
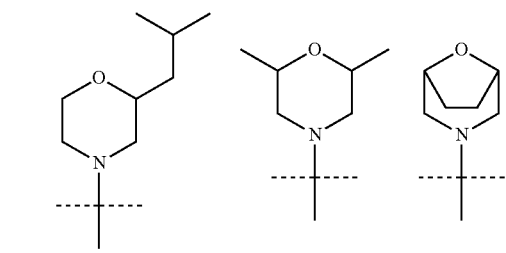
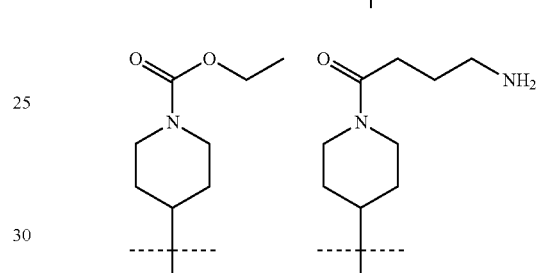
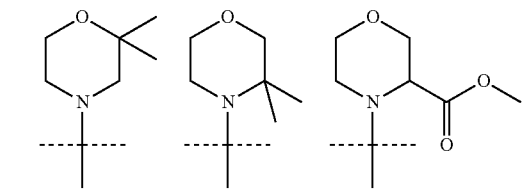
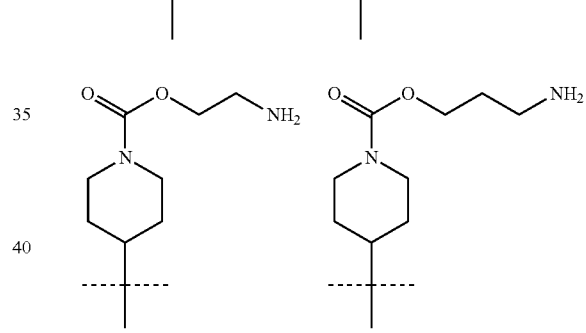
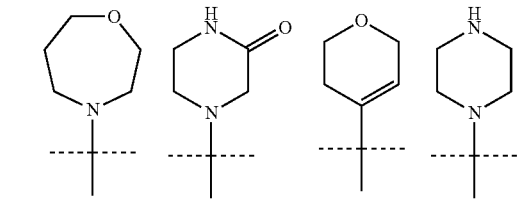
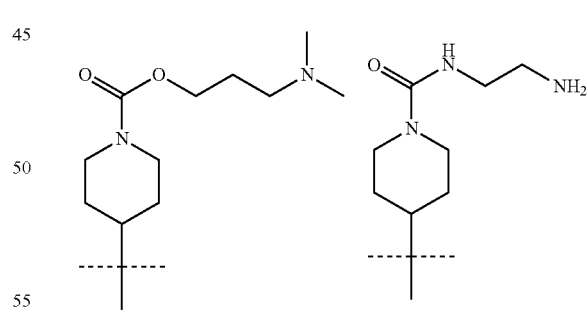
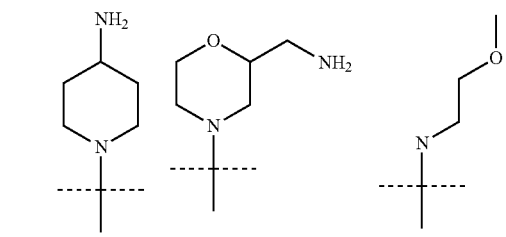
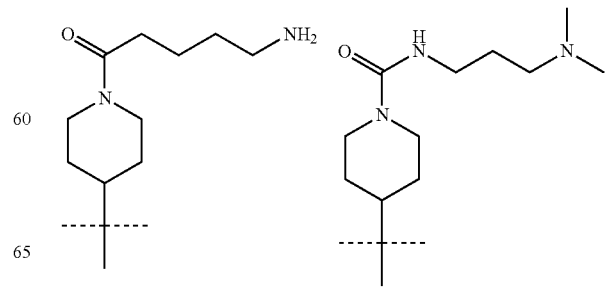

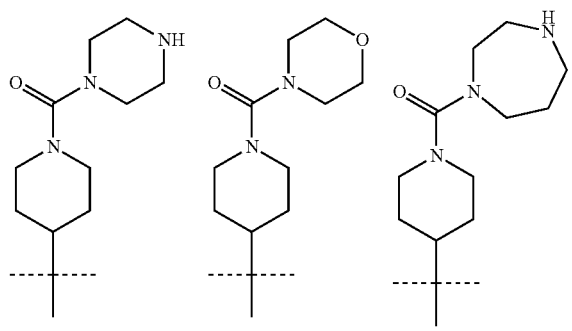
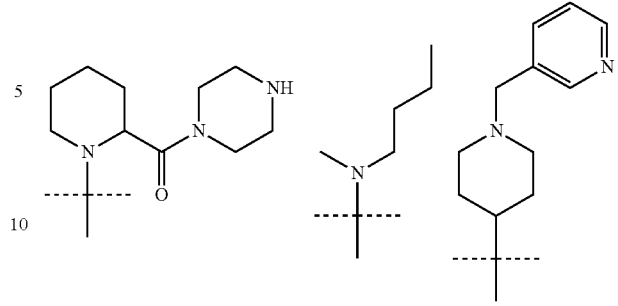
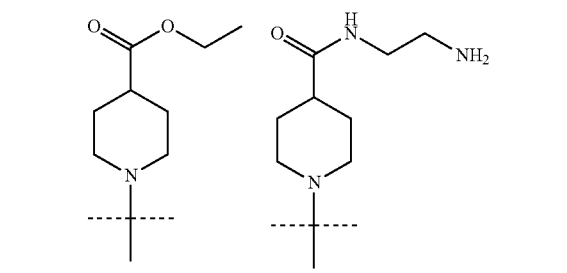
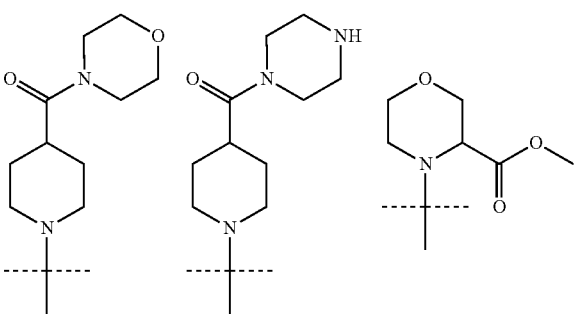
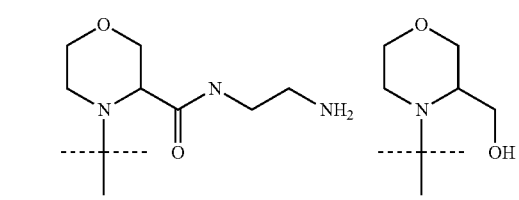
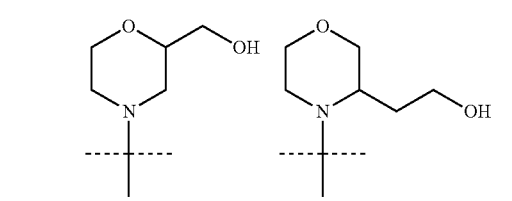
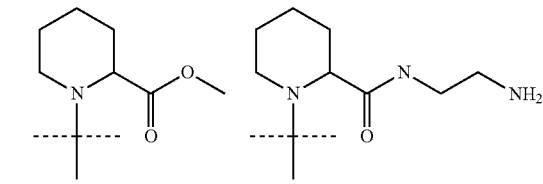

Embodiments of the invention include:
4-[2-(6-Aminopyridin-3-yl)-1-(4-chlorophenyl)-1H-pyrrolo[2,3-c]pyridin-3-yl]piperidine-1-carboxamide;
4-[1-(4-Chlorophenyl)-2-(pyrimidin-5-yl)-1H-pyrrolo[2,3-c]pyridin-3-yl]piperidine-1-carboxamide;
4-[1-(4-Chlorophenyl)-2-(6-methoxypyridin-3-yl)-1H-pyrrolo[2,3-c]pyridin-3-yl]piperidine-1-carboxamide;
4-[1-(4-Chlorophenyl)-2-(2-methoxypyridin-4-yl)-1H-pyrrolo[2,3-c]pyridin-3-yl]piperidine-1-carboxamide;
4-[1-(4-Chlorophenyl)-2-[2-(4-methylpiperazin-1-yl)pyridin-4-yl]-1H-pyrrolo[2,3-c]pyridin-3-yl]piperidine-1-carboxamide;
4-[1-(4-Chlorophenyl)-2-[6-(morpholin-4-yl)pyridin-3-yl]-1H-pyrrolo[2,3-c]pyridin-3-yl]piperidine-1-carboxamide;
4-[1-(4-Chlorophenyl)-2-(pyrimidin-5-yl)-1H-pyrrolo[2,3-c]pyridin-3-yl]piperidine-1-carboxamide;
4-[1-(4-Chlorophenyl)-2-(1H-pyrazol-3-yl)-1H-pyrrolo[2,3-c]pyridin-3-yl]piperidine-1-carboxamide;
4-[1-(4-Chlorophenyl)-2-(1H-pyrazol-4-yl)-1H-pyrrolo[2,3-c]pyridin-3-yl]piperidine-1-carboxamide;
4-[1-(4-Chlorophenyl)-2-(1-methyl-1H-pyrazol-4-yl)-1H-pyrrolo[2,3-c]pyridin-3-yl]piperidine-1-carboxamide;
4-[1-(4-Chlorophenyl)-2-(1-methyl-1H-pyrazol-5-yl)-1H-pyrrolo[2,3-c]pyridin-3-yl]piperidine-1-carboxamide;
4-[1-(4-Chlorophenyl)-2-(1-methyl-1H-imidazol-5-yl)-1H-pyrrolo[2,3-c]pyridin-3-yl]piperidine-1-carboxamide;
4-[1-(4-Chlorophenyl)-2-(1H-pyrazol-1-yl)-1H-pyrrolo[2,3-c]pyridin-3-yl]piperidine-1-carboxamide;
4-[1-(4-Chlorophenyl)-2-(1H-imidazol-1-yl)-1H-pyrrolo[2,3-c]pyridin-3-yl]piperidine-1-carboxamide;
4-[1-(4-Chlorophenyl)-2-(1H-1,2,3-triazol-1-yl)-1H-pyrrolo[2,3-c]pyridin-3-yl]piperidine-1-carboxamide;
4-[1-(4-Chlorophenyl)-2-(1H-1,2,4-triazol-1-yl)-1H-pyrrolo[2,3-c]pyridin-3-yl]piperidine-1-carboxamide;
4-[1-(4-Chlorophenyl)-3-(piperidin-4-yl)-1H-pyrrolo[2,3-c]pyridin-2-yl]pyridine;
5-[1-(4-Chlorophenyl)-3-(piperidin-4-yl)-1H-pyrrolo[2,3-c]pyridin-2-yl]pyridin-2-amine;
{[1-(4-Chlorophenyl)-2-(pyridin-4-yl)-1H-pyrrolo[2,3-c]pyridin-3-yl]methyl}dimethyl amine;
{[1-(4-Chlorophenyl)-2-(pyridin-3-yl)-1H-pyrrolo[2,3-c]pyridin-3-yl]methyl}dimethyl amine; and
4-[1-(4-Chlorophenyl)-2-(2H-1,2,3,4-tetrazol-5-yl)-1H-pyrrolo[2,3-c]pyridin-3-yl]piperidine
and pharmaceutically acceptable salts thereof.

In an embodiment, the invention includes a pharmaceutical composition comprising a compound of formula (I) and pharmaceutically acceptable salts thereof, and one or more suitable excipients.

In an embodiment, the compounds of the invention are for use in the treatment of inflammation, an inflammatory disease, an immune or an autoimmune disorder, or inhibition of tumour growth, or for use in the manufacture of a medicament for treatment of inflammation, an inflammatory disease, an immune or an autoimmune disorder, or inhibition of tumour growth.

In an embodiment the compounds of the invention are useful in a method for the treatment of inflammation, an inflammatory disease, an immune or an autoimmune disorder, or inhibition of tumour growth, which comprises administering to a subject suffering such disease an effective amount of a compound of formula (I).

In an embodiment the inflammation or inflammatory disease or immune or autoimmune disorder is arthritis (including rheumatoid arthritis, juvenile rheumatoid arthritis, osteoarthritis and psoriatic arthritis), synovitis, vasculitis, Sjogren's disease, a condition associated with inflammation of the bowel (including Crohn's disease, ulcerative colitis, inflammatory bowel disease and irritable bowel syndrome), atherosclerosis, multiple sclerosis, Alzheimer's disease, vascular dementia, Parkinson's disease, cerebral amyloid angiopathy, cerebral autosomal dominant arteriopathy with subcortical infarcts and leukoencephalopathy, a pulmonary inflammatory disease (including asthma, chronic obstructive pulmonary disease and acute respiratory distress syndrome), a fibrotic disease (including idiopathic pulmonary fibrosis, cardiac fibrosis, liver fibrosis and systemic sclerosis (scleroderma)), an inflammatory disease of the skin (including contact dermatitis, atopic dermatitis and psoriasis), an inflammatory disease of the eye (including age related macular degeneration, uveitis and diabetic retinopathy), systemic inflammatory response syndrome, sepsis, an inflammatory and/or autoimmune condition of the liver (including autoimmune hepatitis, primary biliary cirrhosis, alcoholic liver disease, sclerosing cholangitis, and autoimmune cholangitis), diabetes (type I or II) and/or the complications thereof, chronic heart failure, congestive heart failure, an ischemic disease (including stroke and ischemia-reperfusion injury) or myocardial infarction and/or the complications thereof, or epliepsy.

In an embodiment the inflammation or inflammatory disease or immune or autoimmune disorder is selected from rheumatoid arthritis, osteoarthritis, liver fibrosis, chronic obstructive pulmonary disease, multiple sclerosis, Sjogren's disease, Alzheimer's disease, Parkinson's disease, inflammatory bowel disease and vascular dementia.

PREPARATION OF COMPOUNDS OF THE INVENTION

The compounds of formula (I) above may be prepared by, or in analogy with, conventional methods. The preparation of intermediates and compounds according to the examples of the present invention may in particular be illuminated by the following Schemes. Definitions of variables in the structures in schemes herein are commensurate with those of corresponding positions in the formulas delineated herein.

Scheme 1. General synthetic routes for preparation of compounds of formula (I)

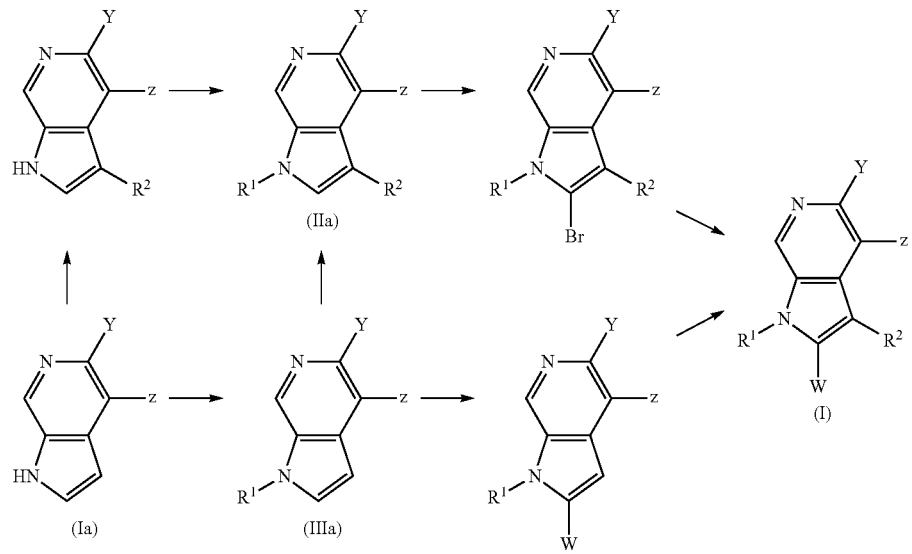

wherein W, Y, Z, Q, $R^1$ and $R^2$ are as defined in formula (I);

Compounds of general formula (I) can easily be prepared from 6-azaindoles (Ia) by either introduction of $R^2$ (or protected $R^2$) followed by introduction of $R^1$ or by reversing these steps to give intermediates of general formula (IIa). Compounds of general formula (IIa) can then be converted to compounds of general formula (I) by for example, bromination and subsequent aryl coupling. Alternatively, compounds of general formula (I) can be prepared from compounds of intermediate (IIIa) by introduction of W followed by introduction of $R^2$ by standard synthetic methods.

Optionally, the group R2 can be transformed into another group $R^2$ and if required, standard protecting group strategies can be employed to facilitate the synthesis.

Optionally, a compound of formula (I) can also be transformed into another compound of formula (I) in one or more synthetic steps.

Scheme 2 illustrates how the compounds of general formula (I) may be prepared.

Scheme 2. Example preparations of compounds of formula (I)
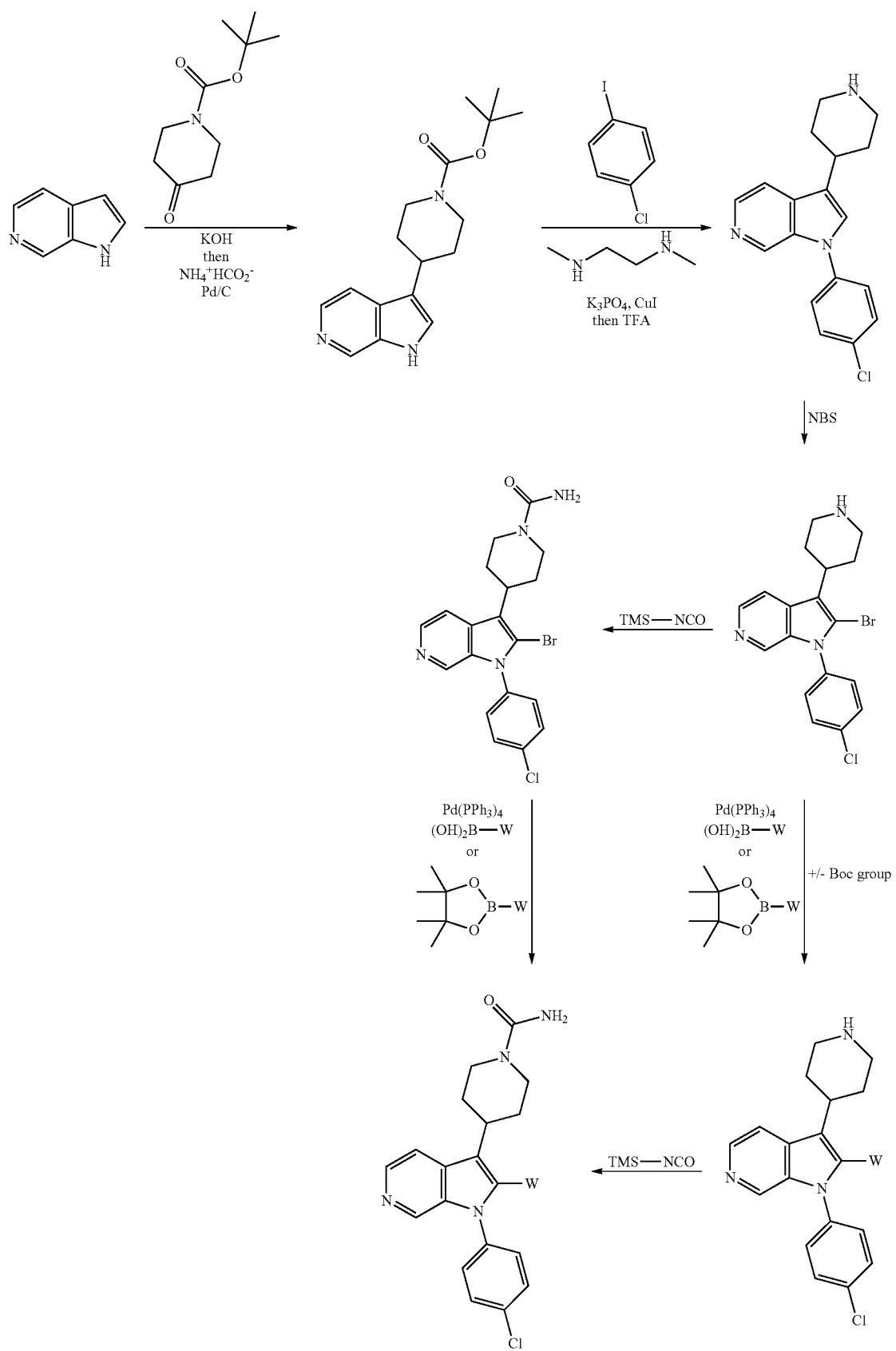

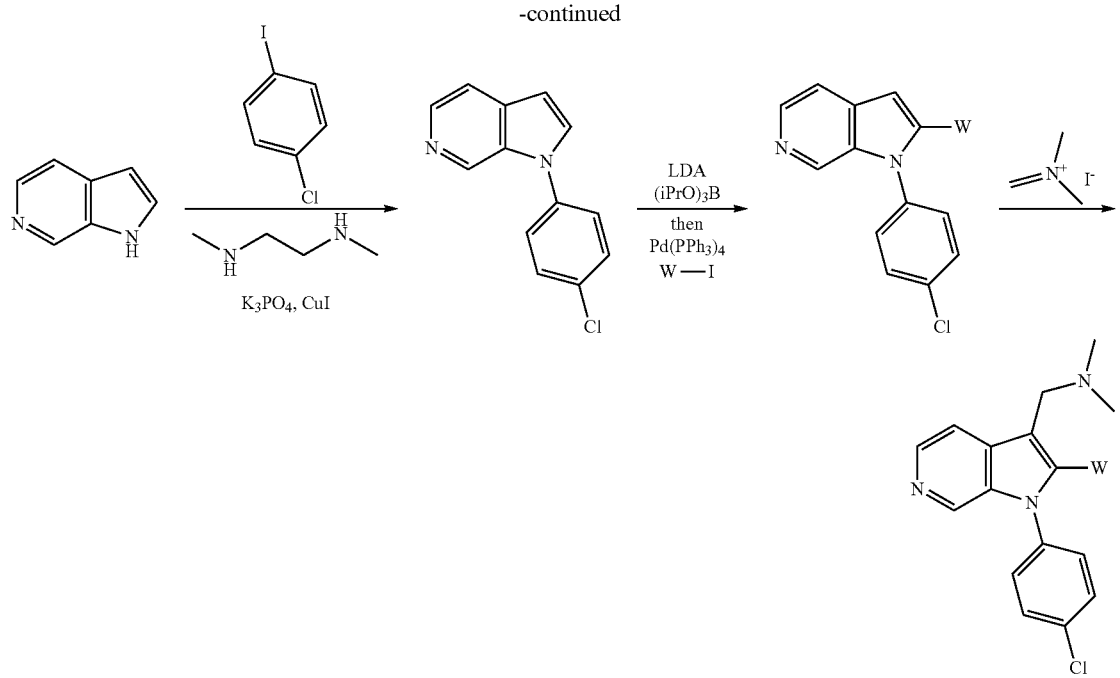

The following abbreviations have been used:
aq aqueous
Boc tertiary-butyloxycarbonyl
calcd Calculated
conc concentrated
d day(s)
DCM dichloromethane
DIPEA diisopropylethylamine
DMA dimethylacetamide
DMAP 4-dimethylaminopyridine
DMF dimethylformamide
DMSO Dimethyl sulfoxide
dppf 1,1'-bis(diphenylphosphino)ferrocene
ESI+ electrospray ionization
Et₃N triethylamine
EtOAc ethyl acetate
EtOH ethanol
Ex Example
h hour(s)
HPLC High Performance Liquid Chromatography
HRMS High-Resolution Mass Spectrometry
Int Intermediate
LCMS Liquid Chromatography Mass Spectrometry
LDA Lithium diisopropylamide
M molar
MeCN acetonitrile
MeOH methanol
[MH]+ protonated molecular ion
min minute(s)
MS Mass Spectrometry
NBS N-bromosuccinimide
Ph Phenyl
QTOF Quadrupole time-of-flight mass spectrometer
RP Reverse phase
Rt retention time
RT room temperature
sat saturated
TFA trifluoroacetic acid
THF Tetrahydrofuran
UV Ultra violet

EXAMPLES AND INTERMEDIATE COMPOUNDS

Experimental Methods

Reactions were conducted at room temperature unless otherwise specified. Microwave reactions were performed with a Biotage microwave reactor using process vials fitted with aluminium caps and septa. Preparative chromatography was performed using a Flash Master Personal system equipped with Isolute Flash II silica columns or using a CombiFlash Companion system equipped with GraceResolv silica column. Reverse Phase HPLC was performed on a Gilson system with a UV detector equipped with Phenomenex Synergi Hydro RP 150×10 mm, or YMC ODS-A 100/150×20 mm columns. The purest fractions were collected, concentrated and dried under vacuum. Compounds were typically dried in a vacuum oven at 40° C. prior to purity analysis. Compound analysis was performed by HPLC/LCMS using an Agilent 1100 HPLC system/Waters ZQ mass spectrometer connected to an Agilent 1100 HPLC system with a Phenomenex Synergi, RP-Hydro column (150×4.6 mm, 4 um, 1.5 mL per min, 30° C., gradient 5-100% MeCN (+0.085% TFA) in water (+0.1% TFA) over 7 min, 200-300 nm). Accurate masses were measured using a Waters QTOF electrospray ion source and corrected using Leucine Enkephalin lockmass. Spectra were acquired in positive and negative electrospray mode. The acquired mass range was m/z 100-1000. Test compounds were dissolved in DMSO to give a 10 mM stock solution. Typically 5 mL of the DMSO stock were diluted with 495 mL of MeCN and then further diluted with MeCN and water (1:1) to give a final concentration of 0.2 mM. The mass values reported correspond either to the parent molecule with a hydrogen added [MH] or with a hydrogen subtracted [M-H]. The compounds prepared were named using IUPAC nomenclature.

Intermediate 1 tert-Butyl 4-{1H-pyrrolo[2,3-c]pyridin-3-yl}-1,2,3,6-tetrahydropyridine-1-carboxylate

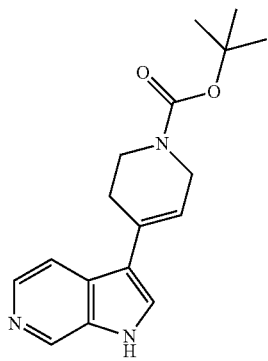 [SMILES: CC(C)(C)OC(=O)N1CC=C(c2c[nH]c3cnccc23)CC1]

6-Azaindole (14.0 g, 117 mmol) was dissolved in MeOH (200 mL) and KOH (14.6 g, 261 mmol) and tert-butyl 4-oxopiperidine-1-carboxylate (26.0 g, 130 mmol) were added. The reaction mixture was heated at 70° C. for 64 h. The reaction mixture was partitioned between DCM (500 mL) and water (200 mL) and the aqueous fraction was extracted with DCM (2×200 mL). The combined organic fractions were dried (MgSO$_4$) and concentrated in vacuo to give the title compound as an orange foam (37.7 g, crude). LCMS (ES$^+$): 300.1 [MH]$^+$. HPLC: Rt 4.72 min, 90.9% purity.

Intermediate 2 tert-Butyl 4-{1H-pyrrolo[2,3-c]pyridin-3-yl}piperidine-1-carboxylate

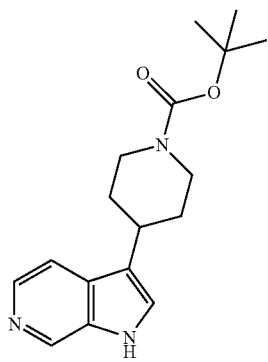 [SMILES: CC(C)(C)OC(=O)N1CCC(c2c[nH]c3cnccc23)CC1]

Intermediate 1 (34.1 g, 114 mmol) and ammonium formate (35.9 g, 569 mmol) were dissolved in EtOH (500 mL) and 10% palladium on carbon (2.00 g) was added. The reaction mixture was heated at reflux for 2 h, filtered through Celite and concentrated in vacuo. The residue was dissolved in water (500 mL) and extracted with DCM (3×500 mL). The combined organic fractions were dried (MgSO$_4$) and concentrated in vacuo to give the title compound as a yellow solid (30.7 g, 89.5%). LCMS (ES$^+$): 302.1 [MH]$^+$. HPLC: Rt 4.70 min, 86.1% purity.

Intermediate 3 tert-Butyl 4-[1-(4-chlorophenyl)-1H-pyrrolo[2,3-c]pyridin-3-yl]piperidine-1-carboxylate

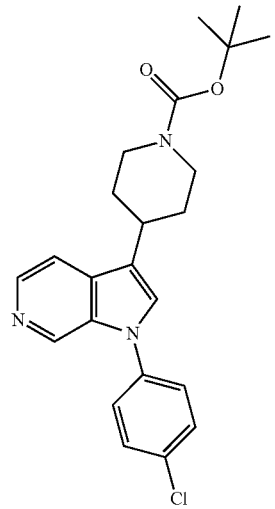 [SMILES: CC(C)(C)OC(=O)N1CCC(c2cn(-c3ccc(Cl)cc3)c3cnccc23)CC1]

Intermediate 2 (50.7 g, 168 mmol), 1-chloro-4-iodobenzene (48.1 g, 202 mmol), N,N-dimethylethylenediamine (3.62 mL, 33.6 mmol), K$_3$PO$_4$ (75.0 g, 353 mmol) and CuI (3.20 g, 16.8 mmol) were suspended in DMF (1.01 L) under N$_2$ and heated at 137° C. for 24 h. The reaction mixture was concentrated in vacuo, dissolved in water (600 mL) and EtOAc (600 mL) and filtered through Celite. The organic fraction was washed with water (2×250 mL) and concentrated in vacuo. The residue was slurried in EtOAc (450 mL) at 45° C. for 30 min, cooled to 0° C. for 30 min and the resulting precipitate was collected by filtration and washed with EtOAc (50 mL) to give the title compound (22.4 g, 32.3%) as a light brown solid. HPLC: Rt 3.16 min, 97.2% purity.

Intermediate 4

4-[1-(4-Chlorophenyl)-1H-pyrrolo[2,3-c]pyridin-3-yl]piperidine

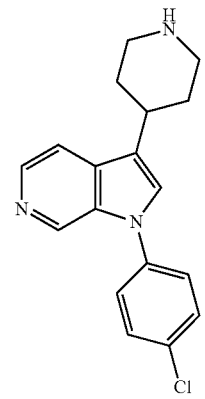 [SMILES: Clc1ccc(-n2cc(C3CCNCC3)c3ccncc32)cc1]

Intermediate 3 (35.6 g, 86.3 mmol) was dissolved in DCM (178 mL), TFA (40 mL, 518 mmol) was added and the reaction mixture was stirred overnight. DCM (150 mL) and 2M aq. NaOH (270 mL) were added and the reaction mixture was stirred for 1 h. The organic fraction was concentrated in vacuo and slurried in EtOAc (40 mL) and heptane (250 mL) for 20 min. The resulting precipitate was collected by filtration and washed with heptane (50 mL) to give the title compound as a light brown solid (26.3 g, 97.6%). LCMS (ES$^+$): 312.0 [MH]$^+$. HPLC: Rt 3.63 min, 99.2% purity.

Intermediate 5

4-[2-Bromo-1-(4-chlorophenyl)-1H-pyrrolo[2,3-c]pyridin-3-yl]piperidine

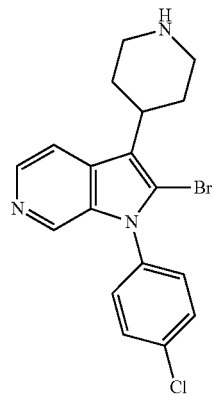 [SMILES: Clc1ccc(-n2c(Br)c(C3CCNCC3)c3ccncc32)cc1]

Intermediate 4 (10.0 g, 32.1 mmol) was dissolved in conc. aq. H$_2$SO$_4$ (250 mL) and NBS (7.99 g, 44.9 mmol) was added. The reaction mixture was stirred for 3 h, diluted with water (1 L), basified with Na$_2$CO$_3$ and extracted into DCM (3×1 L). The combined organic fractions were dried (MgSO$_4$) and concentrated in vacuo. The residue was purified by column chromatography to give the title compound as an orange gum (5.79 g, 46.2%). LCMS (ES$^+$): 390.1 [MH]$^+$. HPLC: Rt 3.83 min, 85.6% purity.

Intermediate 6

4-[2-Bromo-1-(4-chlorophenyl)-1H-pyrrolo[2,3-c]pyridin-3-yl]piperidine-1-carboxamide

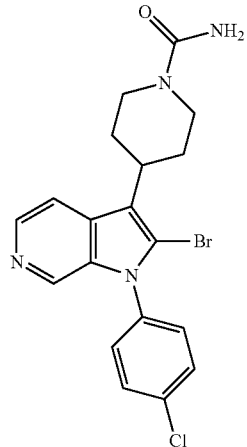 [SMILES: NC(=O)N1CCC(c2c(Br)n(-c3ccc(Cl)cc3)c3cnccc23)CC1]

Intermediate 5 (1.57 g, 4.02 mmol) and DIPEA (1.05 mL, 6.03 mmol) were dissolved in DCM (40 mL) and trimethylsilylisocyanate (817 uL, 6.03 mmol) was added. The reaction mixture was stirred for 18 h, diluted with 1M aq. Na$_2$CO$_3$ (100 mL) and extracted into DCM (3×100 mL). The combined organic fractions were dried (MgSO$_4$) and concentrated in vacuo. The residue was purified by column chromatography to give the title compound as a yellow solid (1.56 g, 89.6%). LCMS (ES$^+$): 433.0, 435.0 [MH]$^+$. HPLC: Rt 4.72 min, 85.0% purity.

Intermediate 7 tert-Butyl 4-[2-bromo-1-(4-chlorophenyl)-1H-pyrrolo[2,3-c]pyridin-3-yl]piperidine-1-carboxylate

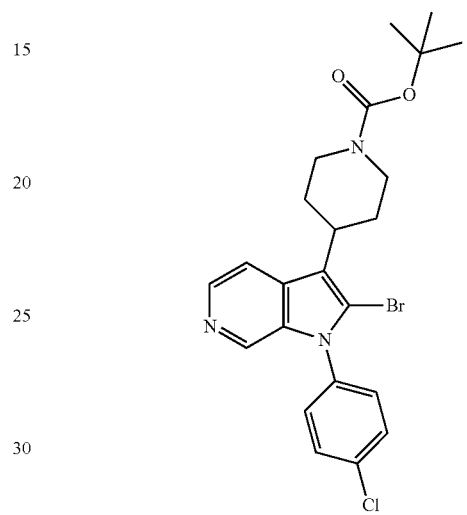

Intermediate 5 (3.19 g, 8.16 mmol) was dissolved in DCM (50 mL), Et$_3$N (1.19 mL, 8.57 mmol), DMAP (49.9 mg, 0.408 mmol) and Boc$_2$O (1.87 g, 8.57 mmol) were added and the reaction mixture was stirred for 20 h. The reaction mixture was washed with water (2×50 mL), dried (MgSO$_4$) and concentrated in vacuo. The residue was purified by column chromatography to give the title compound (3.29 g, 82.1%) as a yellow foam. LCMS (ES$^+$): 490.1, 492.1, 494.1 [MH]$^+$. HPLC: Rt 6.26 min, 90.0% purity.

Intermediate 8

4-[1-(4-Chlorophenyl)-2-(1-methyl-1H-pyrazol-5-yl)-1H-pyrrolo[2,3-c]pyridin-3-yl]piperidine

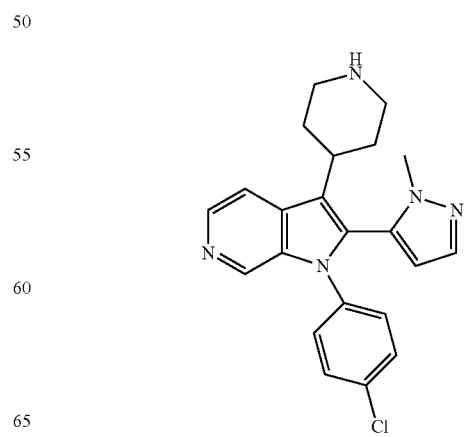

Intermediate 7 (250 mg, 0.509 mmol), 1-methylpyrazole-5-boronic acid neopentyl glycol ester (148 mg, 0.764 mmol) and Na₂CO₃ (162 mg, 1.53 mmol) were dissolved in dioxane (4 mL) and water (1 mL) under N₂. Pd(PPh₃)₄ (124 mg, 0.107 mmol) was added and the reaction mixture was heated using a microwave reactor at 100° C. for 90 min. The reaction mixture was diluted with water (40 mL) and extracted with DCM (40 mL). The organic fraction was washed with water (25 mL), dried (MgSO₄) and concentrated in vacuo. The residue was purified by column chromatography, dissolved in 1.25M HCl in EtOH (10 mL) and stirred overnight. The reaction mixture was concentrated in vacuo and the residue was purified by column chromatography to give the title compound as a yellow gum (132 mg, 52.7%). LCMS (ES⁺): 392.2 [MH]⁺. HPLC: Rt 4.13 min, 95.1% purity.

Intermediate 9

4-[1-(4-Chlorophenyl)-2-(1-methyl-1H-imidazol-5-yl)-1H-pyrrolo[2,3-c]pyridin-3-yl]piperidine trihydrochloride

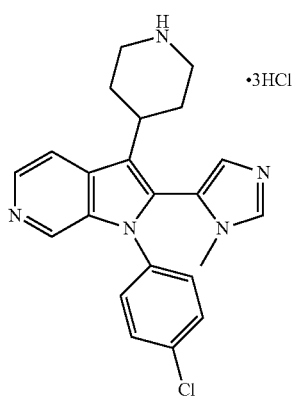 [SMILES: Cn1cncc1-c1c(C2CCNCC2)c2ccncc2n1-c1ccc(Cl)cc1]

Intermediate 9 was prepared similarly to Intermediate 8, using 1-methyl-5-(tetramethyl-1,3,2-dioxaborolan-2-yl)-1H-imidazole instead of 1-methylpyrazole-5-boronic acid neopentyl glycol ester, to give the title compound as a yellow gum (40.0 mg, 38.9%). LCMS (ES⁺): 392.2 [MH]⁺ HPLC: Rt 3.15 min, 90.6% purity.

Intermediate 10

4-[1-(4-Chlorophenyl)-2-(1H-pyrazol-1-yl)-1H-pyrrolo[2,3-c]pyridin-3-yl]piperidine

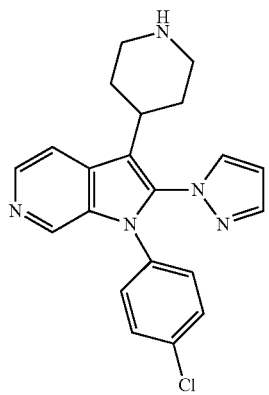 [SMILES: Clc1ccc(-n2c(-n3cccn3)c(C3CCNCC3)c3ccncc32)cc1]

Intermediate 7 (300 mg, 0.611 mmol), pyrazole (83.2 mg, 1.22 mmol), N,N' dimethylethylenediamine (26.3 uL, 0.244 mmol), K₃PO₄ (415 mg, 1.96 mmol) and CuI (23.3 mg, 0.122 mmol) were suspended in DMF (2 mL) under N₂ and heated using a microwave reactor at 160° C. for 1 h. The reaction mixture was partitioned between DCM (50 mL) and water (50 mL), the aqueous fraction was extracted with DCM (50 mL) and the combined organic fractions were dried (MgSO₄) and concentrated in vacuo. The residue was purified by reverse phase HPLC, dissolved in DCM (4 mL) and TFA (1 mL) and the reaction mixture was stirred for 1 h. The reaction mixture was concentrated in vacuo, dissolved in sat aq. NaHCO₃ (10 mL), extracted into DCM (2×10 mL), dried (MgSO₄) and concentrated in vacuo to give the crude title compound (8.00 mg, 3.46%) as a colourless gum. LCMS (ES⁺): 378.2 [MH]⁺.

Intermediates 11-13

Intermediates 11-13 were prepared similarly to Intermediate 10, by CuI coupling of Intermediate 7 with the appropriate N₂ heterocycle, followed by Boc deprotection; see Table 1 below.

TABLE 1
Cul catalysed couplings
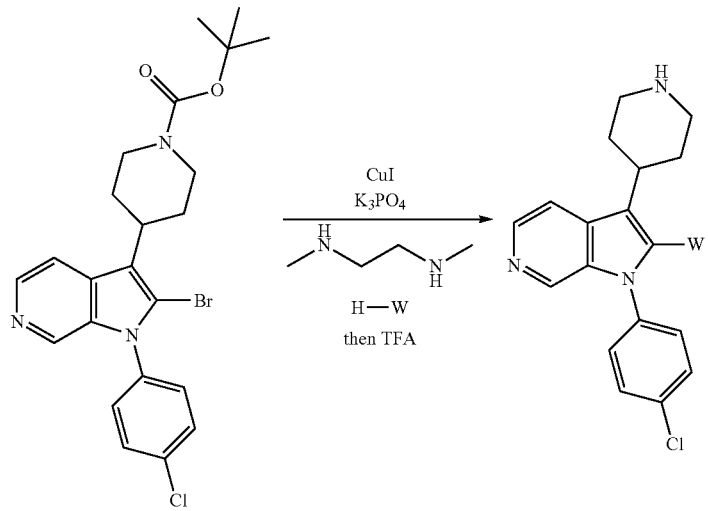
| Int | Structure | Name | Form, Yield, LCMS, HPLC |
|---|---|---|---|
| 11 | 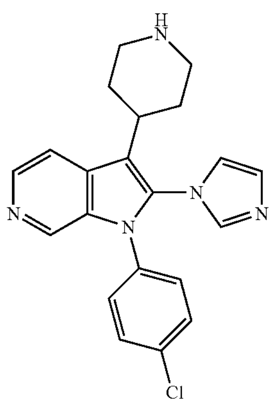 [SMILES: Clc1ccc(-n2c(-n3ccnc3)c(C3CCNCC3)c3ccncc32)cc1] | 4-[1-(4-Chlorophenyl)-2-(1H-imidazol-1-yl)-1H-pyrrolo[2,3-c]pyridin-3-yl]piperidine | Off white solid<br>Yield 26.0 mg, 16.9%<br>LCMS (ES$^+$): 378.2 [MH]$^+$ |
| 12 | 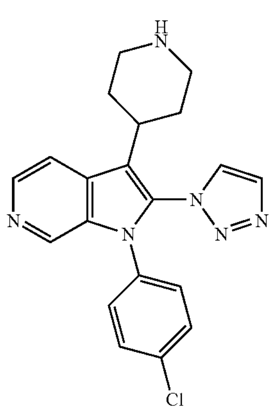 [SMILES: Clc1ccc(-n2c(-n3ccnn3)c(C3CCNCC3)c3ccncc32)cc1] | 4-[1-(4-Chlorophenyl)-2-(1H-1,2,3-triazol-1-yl)-1H-pyrrolo[2,3-c]pyridin-3-yl]piperidine | Pale yellow foam<br>Yield 40.0 mg, crude<br>LCMS (ES$^+$): 379.0 [MN]$^+$<br>HPLC: Rt 3.91 min, 50.3% purity. |

TABLE 1-continued

CuI catalysed couplings

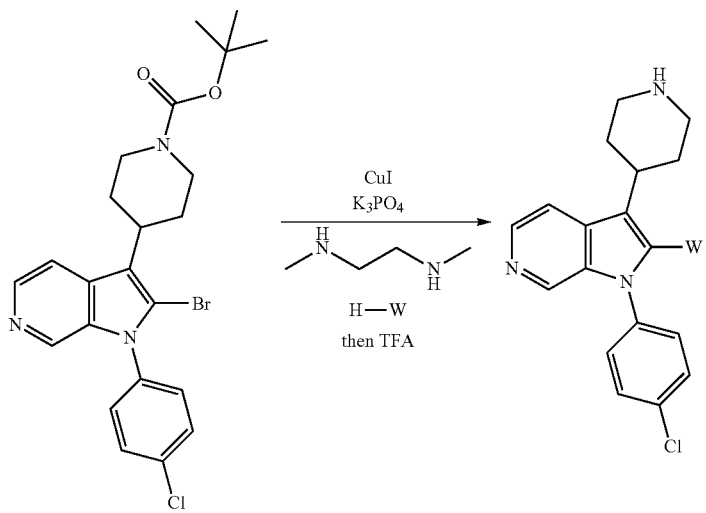

| Int | Structure | Name | Form, Yield, LCMS, HPLC |
|---|---|---|---|
| 13 | 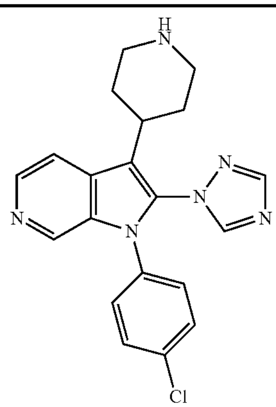 | 4-[1-(4-Chlorophenyl)-2-(1H-1,2,4-triazol-1-yl)-1H-pyrrolo[2,3-c]pyridin-3-yl]piperidine | Pale yellow foam<br>Yield 40.0 mg, 51.8%<br>LCMS (ES+): 379.2 [MN]+<br>HPLC: Rt 3.61 min, 78.1% purity. |

Intermediate 14

1-(4-Chlorophenyl)-1H-pyrrolo[2,3-c]pyridine

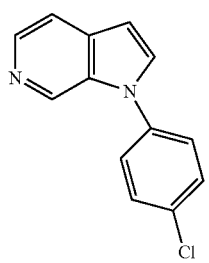 [SMILES: Clc1ccc(-n2ccc3ccncc32)cc1]

6-Azaindole (5.00 g, 42.3 mmol) was dissolved in DMF (150 mL) under $N_2$ and 1-chloro-4-iodo-benzene (12.2 g, 50.8 mmol), N,N-dimethylethylenediamine (911 uL, 8.46 mmol), $K_3PO_4$ (18.9 g, 88.9 mmol) and CuI (806 mg, 4.23 mmol) were added. The reaction mixture was heated at 150° C. for 18 h. The reaction mixture was filtered and the filtrate was concentrated in vacuo. The residue was suspended in 1M aq. $Na_2CO_3$ (250 mL) and extracted into DCM (2×250 mL). The combined organic fractions were dried ($MgSO_4$) and concentrated in vacuo. The residue was purified by column chromatography to give the title compound as a yellow solid (8.58 g, 88.6%). LCMS (ES+): 229.1 [MH]+. HPLC: Rt 4.48 min, 98.6% purity.

Intermediate 15

4-[1-(4-Chlorophenyl)-1H-pyrrolo[2,3-c]pyridin-2-yl]pyridine

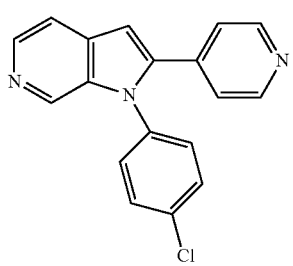 [SMILES: Clc1ccc(-n2c(-c3ccncc3)cc3ccncc32)cc1]

Intermediate 14 (316 mg, 1.38 mmol) and triisopropyl borate (670 uL, 2.90 mmol) were dissolved in THF (5 mL) and the reaction mixture was cooled to 0° C. LDA (1.38 mL, 2.0M in THF/heptane, 2.76 mmol) was added and the reaction mixture was stirred at 0° C. for 30 min. The reaction was quenched with water (2 mL) and diluted with dioxane (3 mL). 4-Iodopyridine (340 mg, 1.66 mmol), Pd(PPh$_3$)$_4$ (128 mg, 0.111 mmol) and a solution of Na$_2$CO$_3$ (439 mg, 4.15 mmol) in water (4 mL) were added. The reaction mixture was heated using a microwave reactor at 160° C. for 20 min. The reaction mixture was partitioned between water (100 mL) and EtOAc (100 mL), and the organic fraction was dried (MgSO$_4$) and concentrated in vacuo. The residue was purified by column chromatography to give the title compound as a yellow oil (372 mg, 88.1%). LCMS (ES$^+$): 306.1 [MH]$^+$.

Intermediate 16

3-[1-(4-Chlorophenyl)-1H-pyrrolo[2,3-c]pyridin-2-yl]pyridine

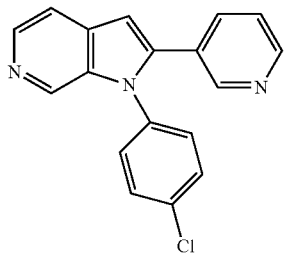 [SMILES: Clc1ccc(-n2c(-c3cccnc3)cc3ccncc32)cc1]

Intermediate 16 was prepared similarly to Intermediate 15, using 3-bromopyridine instead of 4-iodopyridine, to give the title compound as a yellow oil (420 mg, 94.0%). LCMS (ES$^+$): 306.1 [MH]$^+$.

Intermediate 17 tert-Butyl 4-[1-(4-chlorophenyl)-2-cyano-1H-pyrrolo[2,3-c]pyridin-3-yl]piperidine-1-carboxylate

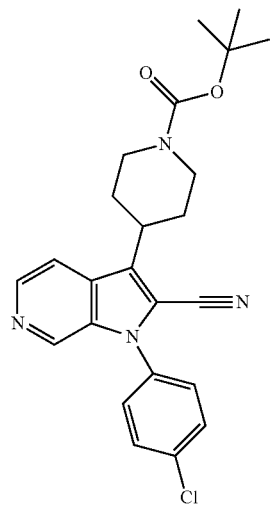 [SMILES: CC(C)(C)OC(=O)N1CCC(c2c(C#N)n(-c3ccc(Cl)cc3)c3cnccc23)CC1]

Intermediate 7 (3.40 g, 6.92 mmol) was dissolved in DMA (60 mL) under N$_2$ and zinc dust (88.6 mg, 1.38 mmol), zinc cyanide (813 mg, 6.92 mmol) and PdCl$_2$(dppf) (CH$_3$)$_2$CO (548 mg, 0.69 mmol) were added. The reaction mixture was heated at 120° C. for 3 h, diluted with EtOAc (300 mL), washed with water (3×200 mL), dried (MgSO$_4$) and concentrated in vacuo. The residue was purified by column chromatography to give the title compound as a white solid (2.02 g, 66.8%). LCMS (ES$^+$): 437.2 [MH]$^+$. HPLC: Rt 5.93 min, 97.2% purity.

Example 1

4-[2-(6-Aminopyridin-3-yl)-1-(4-chlorophenyl)-1H-pyrrolo[2,3-c]pyridin-3-yl]piperidine-1-carboxamide

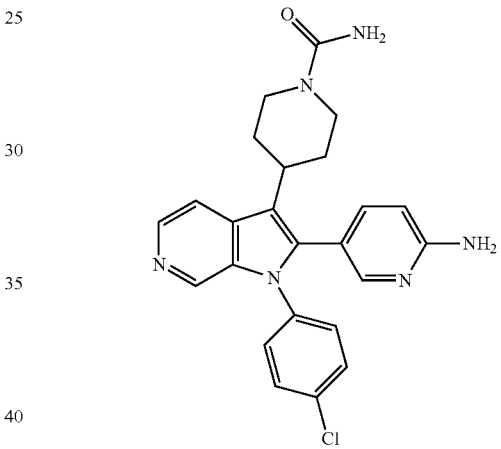

Intermediate 6 (150 mg, 0.346 mmol), 5-(tetramethyl-1,3,2-dioxaborolan-2-yl)pyridin-2-amine (83.7 mg, 0.380 mmol) and Na$_2$CO$_3$ (110 mg, 1.04 mmol) were dissolved in dioxane (4 mL) and water (1 mL) under N$_2$. Pd(PPh$_3$)$_4$ (59.9 mg, 51.9 umol) was added and the reaction mixture was heated using a microwave reactor at 100° C. for 45 min. The reaction mixture was diluted with water (50 mL) and extracted with DCM (3×50 mL). The combined organic fractions were dried (MgSO$_4$) and concentrated in vacuo. The residue was purified by column chromatography and by reverse phase HPLC to give the title compound as a white solid (19.5 mg, 12.6%). HRMS (ESI$^+$) calcd for [MH]$^+$ of C$_{24}$H$_{23}$ClN$_6$O, 447.1700. found 447.1707. HPLC: Rt 3.46 min, 97.8% purity.

Examples 2-10

Examples 2-10 were prepared similarly to Example 1, by Pd(PPh$_3$)$_4$ coupling of Intermediate 6 with the appropriate boronic acid or boronic ester; see Table 2 below.

TABLE 2

Pd(PPh3)4 catalysed couplings

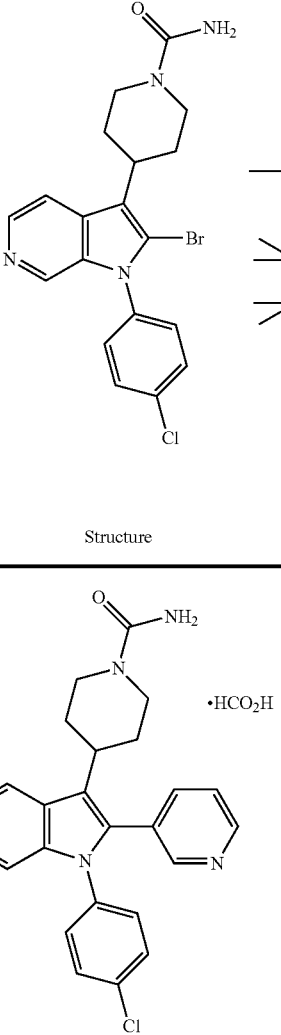

| Ex | Structure | Name | Form, Yield, LCMS, HPLC |
|---|---|---|---|
| 2 | 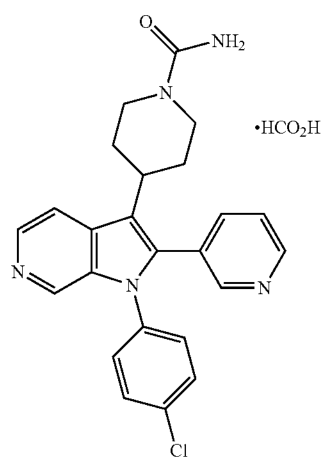 [SMILES: NC(=O)N1CCC(c2c(-c3cccnc3)n(-c3ccc(Cl)cc3)c3cnccc23)CC1 ; "·HCO2H"] | 4-[1-(4-Chlorophenyl)-2-(pyridin-3-yl)-1H-pyrrolo[2,3-c]pyridin-3-yl]piperidine-1-carboxamide; formic acid | White solid Yield 12.7 mg, 5.78% HRMS (ESI+) calcd for [MH]+ of $C_{24}H_{22}ClN_5O$ 432.1591 found 432.1595. HPLC: Rt 4.29 min, 96.0% purity. |
| 3 | 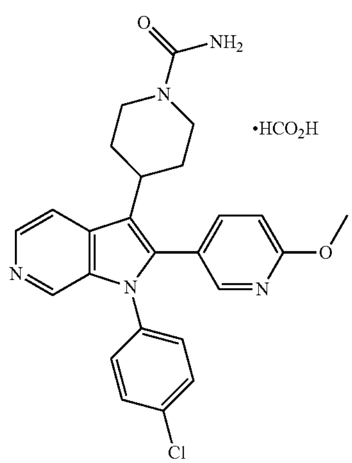 | 4-[1-(4-Chlorophenyl)-2-(6-methoxypyridin-3-yl)-1H-pyrrolo[2,3-c]pyridin-3-yl]piperidine-1-carboxamide; formic acid | White solid Yield 15.1 mg, 6.45% HRMS (ESI+) calcd for [MH]+ of $C_{25}H_{24}ClN_5O_2$ 462.1697 found 462.1707. HPLC: Rt 4.94 min, 99.0% purity. |

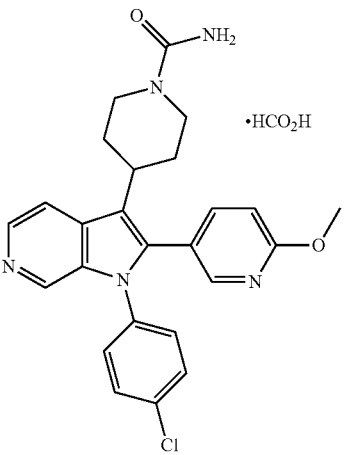 [SMILES: COc1ccc(-c2c(C3CCN(C(N)=O)CC3)c3ccncc3n2-c2ccc(Cl)cc2)cn1 ; "·HCO2H"]

TABLE 2-continued

Pd(PPh$_3$)$_4$ catalysed couplings

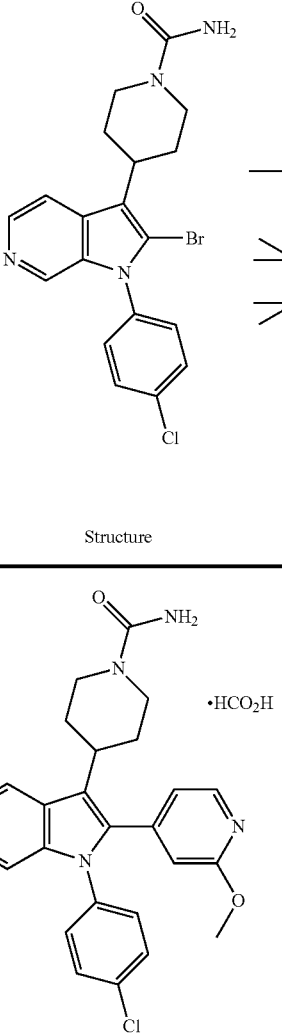

| Ex | Structure | Name | Form, Yield, LCMS, HPLC |
|---|---|---|---|
| 4 | 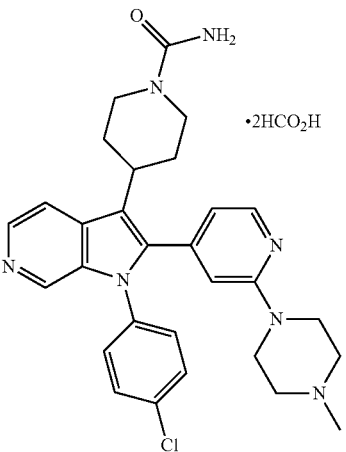 | 4-[1-(4-Chlorophenyl)-2-(2-methoxypyridin-4-yl)-1H-pyrrolo[2,3-c]pyridin-3-yl]piperidine-1-carboxamide; formic acid | White solid Yield 30.1 mg, 12.8% HRMS (ESI$^+$) calcd for [MH]$^+$ of C$_{25}$H$_{24}$ClN$_5$O$_2$ 462.1697 found 462.1710. HPLC: Rt 4.82 min, 96.0% purity. |
| 5 | 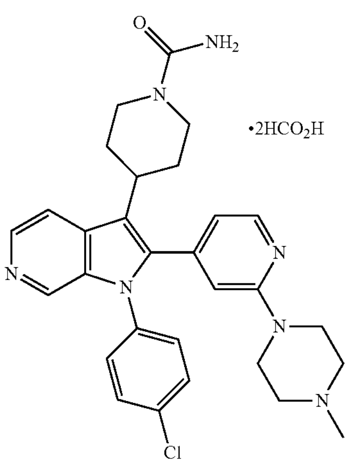 [SMILES: CN1CCN(c2cc(-c3c(C4CCN(C(N)=O)CC4)c4ccncc4n3-c3ccc(Cl)cc3)ccn2)CC1 ; "·2HCO2H"] | 4-[1-(4-Chlorophenyl)-2-[2-(4-methylpiperazin-1-yl)pyridin-4-yl]-1H-pyrrolo[2,3-c]pyridin-3-yl]piperidine-1-carboxamide; bis(formic acid) | White solid Yield 45.0 mg, 18.7% HRMS (ESI$^+$) calcd for [MH]$^+$ of C$_{29}$H$_{32}$ClN$_7$O 530.2435 found 530.2436. HPLC: Rt 4.06 min, 97.2% purity. |

TABLE 2-continued

Pd(PPh$_3$)$_4$ catalysed couplings

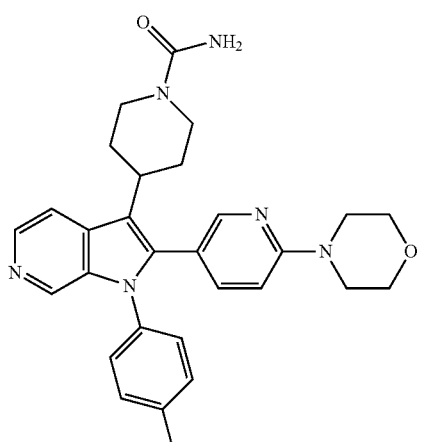

| Ex | Structure | Name | Form, Yield, LCMS, HPLC |
|---|---|---|---|
| 6 | | 4-[1-(4-Chlorophenyl)-2-[6-(morpholin-4-yl)pyridin-3-yl]-1H-pyrrolo[2,3-c]pyridin-3-yl]piperidine-1-carboxamide | Yellow solid Yield 48.2 mg, 20.2% HRMS (ES1$^+$) calcd for [MH]$^+$ of C$_{28}$H$_{29}$ClN$_6$O$_2$ 517.2119 found 517.2124. HPLC: Rt 4.26 min, 97.5% purity. |
| 7 | | 4-[1-(4-Chlorophenyl)-2-(pyrimidin-5-yl)-1H-pyrrolo[2,3-c]pyridin-3-yl]piperidine-1-carboxamide | White solid Yield 23.6 mg, 11.8% HRMS (ESI$^+$) calcd for [MH]$^+$ of C$_{23}$H$_{21}$ClN$_6$O 433.1544 found 433.1548. HPLC: Rt 4.13 min, 100% purity |

TABLE 2-continued

Pd(PPh₃)₄ catalysed couplings

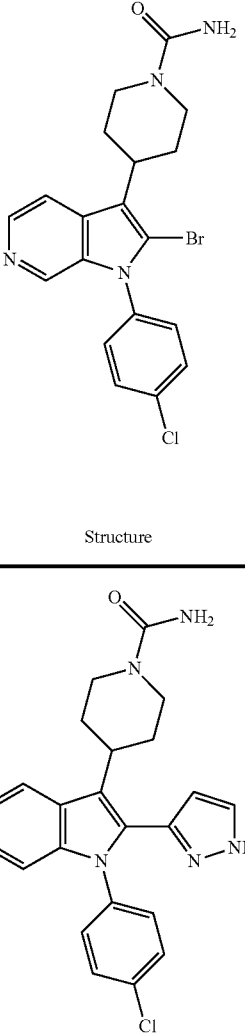

| Ex | Structure | Name | Form, Yield, LCMS, HPLC |
|----|-----------|------|--------------------------|
| 8 | 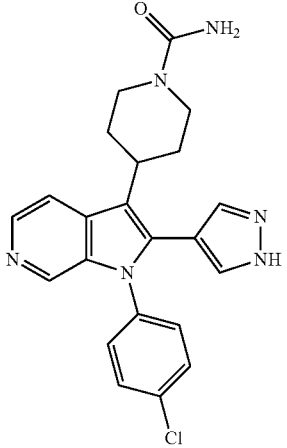 | 4-[1-(4-Chlorophenyl)-2-(1H-pyrazol-3-yl)-1H-pyrrolo[2,3-c]pyridin-3-yl]piperidine-1-carboxamide | White solid Yield 20.5 mg, 3.83% HRMS (ESI⁺) calcd for [MH]⁺ of $C_{22}H_{21}ClN_6O$ 421.1544 found 421.1545. HPLC: Rt 4.21 min, 98.8% purity |
| 9 | 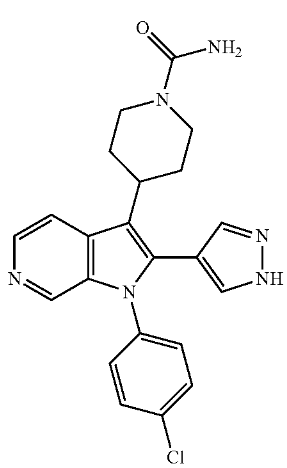 [SMILES: NC(=O)N1CCC(c2c(-c3cn[nH]c3)n(-c3ccc(Cl)cc3)c3cnccc23)CC1] | 4-[1-(4-Chlorophenyl)-2-(1H-pyrazol-4-yl)-1H-pyrrolo[2,3-c]pyridin-3-yl]piperidine-1-carboxamide | White solid Yield 13.2 mg, 6.80% HRMS (ESI⁺) calcd for [MH]⁺ of $C_{22}H_{21}ClN_6O$ 421.1544 found 421.1544. HPLC: Rt 4.03 min, 99.8% purity. |

TABLE 2-continued

Pd(PPh₃)₄ catalysed couplings

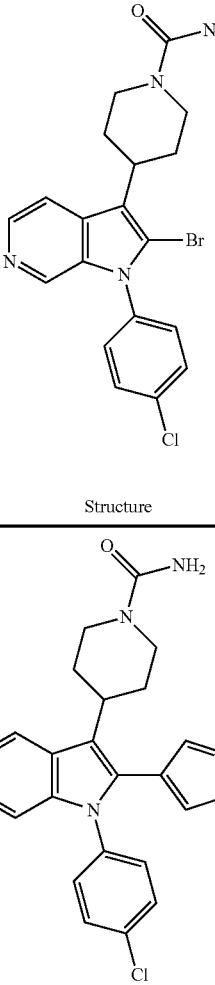

| Ex | Structure | Name | Form, Yield, LCMS, HPLC |
|---|---|---|---|
| 10 | 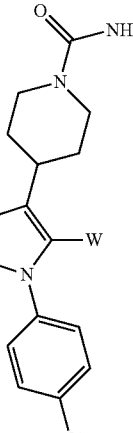 | 4-[1-(4-Chlorophenyl)-2-(1-methyl-1H-pyrazol-4-yl)-1H-pyrrolo[2,3-c]pyridin-3-yl]piperidine-1-carboxamide; trifluoroacetic acid | White solid Yield 7.10 mg, 2.80% HRMS (ESI⁺) calcd for [MH]⁺ $C_{23}H_{23}ClN_6O$ 435.1700 found 435.1706. HPLC: Rt 4.39 min, 97.6% purity. |

Example 11

4-[1-(4-Chlorophenyl)-2-(1-methyl-1H-pyrazol-5-yl)-1H-pyrrolo[2,3-c]pyridin-3-yl]piperidine-1-carboxamide

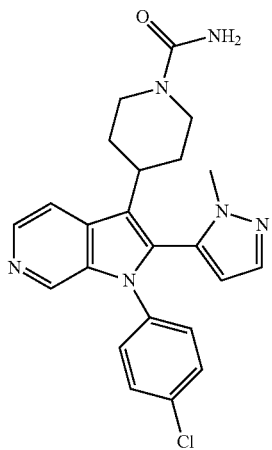 [SMILES: Cn1nccc1-c1c(C2CCN(C(N)=O)CC2)c2ccncc2n1-c1ccc(Cl)cc1]

Intermediate 8 (84.0 mg, 0.214 mmol) and DIPEA (74.7 uL, 0.429 mmol) were dissolved in DCM (6 mL) and trimethylsilyl isocyanate (34.8 uL, 0.257 mmol) was added. The reaction mixture was stirred for 20 h, washed with sat aq. NH₄Cl (3×25 mL), dried (MgSO₄) and concentrated in vacuo. The residue was purified by reverse phase HPLC to give the title compound as a white solid (46.6 mg, 50.0%).

HRMS (ESI⁺) calcd for [MH]⁺ of $C_{23}H_{23}ClN_6O$, 435.1700. found 435.1698. HPLC: Rt 4.37 min, 97.4% purity.

Examples 12-16

Examples 12-16 were prepared similarly to Example 11, by coupling of Intermediates 9-13 with trimethylsilyl isocyanate; see Table 3 below.

TABLE 3

Urea formations

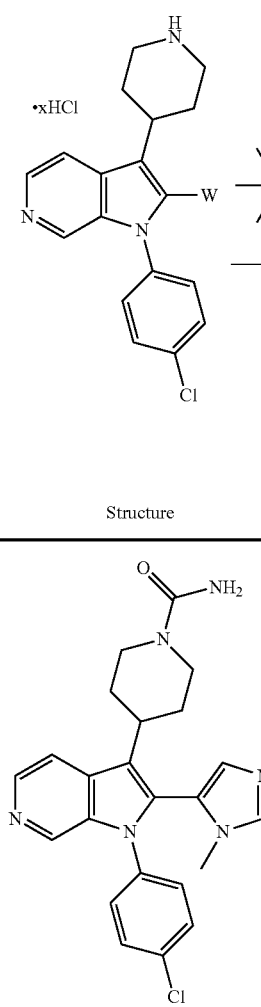

| Ex | Structure | Name | Intermediate used, Form, Yield, LCMS, HPLC |
|---|---|---|---|
| 12 | 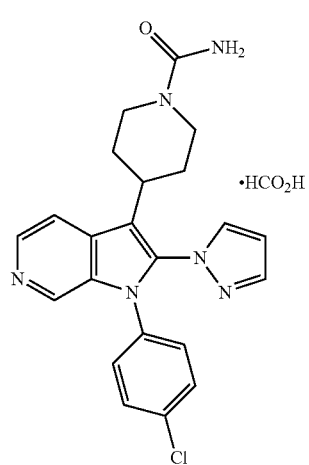 | 4-[1-(4-Chlorophenyl)-2-(1-methyl-1H-imidazol-5-yl)-1H-pyrrolo[2,3-c]pyridin-3-yl]piperidine-1-carboxamide | From Intermediate 9<br>White solid<br>Yield 7.85 mg, 22.6%<br>HRMS (ESI$^+$) calcd for [MH]$^+$ of $C_{23}H_{23}ClN_6O$ 435.1700 found 435.1699.<br>HPLC: Rt 3.30 min, 100% purity. |
| 13 | 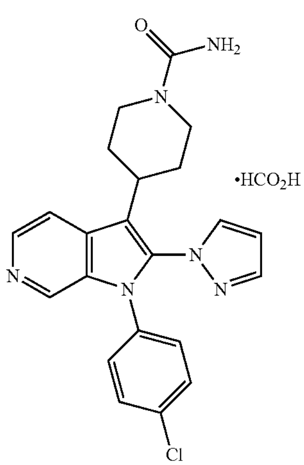 [SMILES: NC(=O)N1CCC(c2c(-n3cccn3)n(-c3ccc(Cl)cc3)c3cnccc23)CC1 ; "·HCO2H"] | 4-[1-(4-Chlorophenyl)-2-(1H-pyrazol-1-yl)-1H-pyrrolo[2,3-c]pyridin-3-yl]piperidine-1-carboxamide; formic acid | From Intermediate 10<br>Colourless gum<br>Yield 5.43 mg, 54.9%<br>HRMS (ESI$^+$) calcd for [MH]$^+$ of $C_{22}H_{21}ClN_6O$ 421.1544 found 421.1546.<br>HPLC: Rt 4.42 min, 98.0% purity. |

TABLE 3-continued

Urea formations

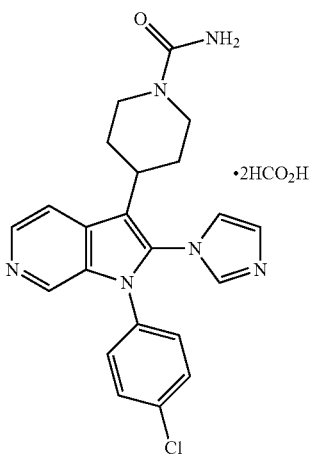 [SMILES: NC(=O)N1CCC(c2c(-n3ccnc3)n(-c3ccc(Cl)cc3)c3cnccc23)CC1 ; "·2HCO2H"]

| Ex | Structure | Name | Intermediate used, Form, Yield, LCMS, HPLC |
|---|---|---|---|
| 14 | 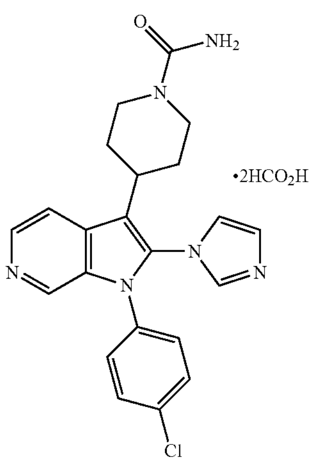 | 4-[1-(4-Chlorophenyl)-2-(1H-imidazol-1-yl)-1H-pyrrolo[2,3-c]pyridin-3-yl]piperidine-1-carboxamide; bis(formic acid) | From Intermediate 11 Colourless gum Yield 22.0 mg, 62.3% HRMS (ESI$^+$) calcd for [MH]$^+$ of $C_{22}H_{21}ClN_6O$ 421.1544 found 421.1534. HPLC: Rt 3.42 min, 99.3% purity. |
| 15 | 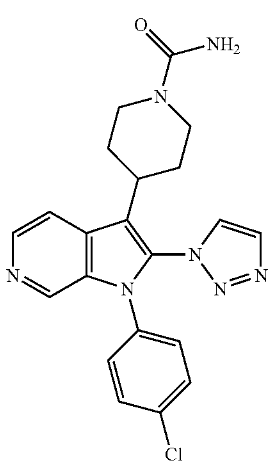 [SMILES: NC(=O)N1CCC(c2c(-n3ccnn3)n(-c3ccc(Cl)cc3)c3cnccc23)CC1] | 4-[1-(4-Chlorophenyl)-2-(1H-1,2,3-triazol-1-yl)-1H-pyrrolo[2,3-c]pyridin-3-yl]piperidine-1-carboxamide | From Intermediate 12 Off white solid Yield 3.34 mg, 7.50% HRMS (ESI$^+$) calcd for [MH]$^+$ of $C_{12}H_{20}ClN_7O$ 422.1496 found 422.1496. HPLC: Rt 4.46 min, 98.6% purity. |

TABLE 3-continued

Urea formations

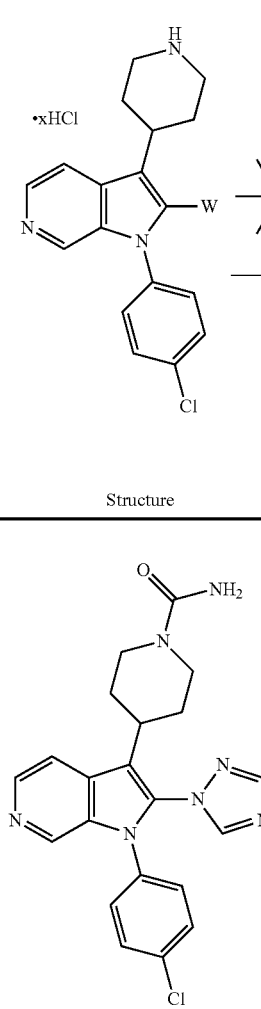

| Ex | Structure | Name | Intermediate used, Form, Yield, LCMS, HPLC |
|---|---|---|---|
| 16 | (structure shown) | 4-[1-(4-Chlorophenyl)-2-(1H-1,2,4-triazol-1-yl)-1H-pyrrolo[2,3-c]pyridin-3-yl]piperidine-1-carboxamide | From Intermediate 13 Off white solid Yield 9.41 mg, 21.1% HRMS (ESI$^+$) calcd for [MH]$^+$ of $C_{21}H_{20}ClN_7O$ 422.1496 found 422.1502. HPLC: Rt 4.04 min, 97.0% purity. |

Example 17

4-[1-(4-Chlorophenyl)-3-(piperidin-4-yl)-1H-pyrrolo[2,3-c]pyridin-2-yl]pyridine

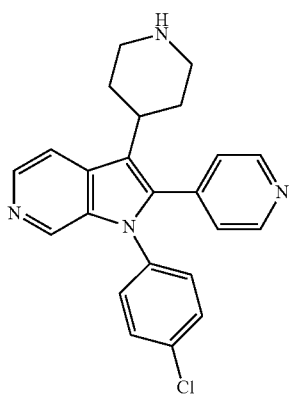 [SMILES: Clc1ccc(-n2c(-c3ccncc3)c(C3CCNCC3)c3ccncc32)cc1]

Intermediate 7 (300 mg, 0.611 mmol), 4-pyridineboronic acid pinacol ester (134 mg, 0.672 mmol) and Na$_2$CO$_3$ (194 mg, 1.83 mmol) were dissolved in dioxane (4 mL) and water (1 mL) under N$_2$. Pd(PPh$_3$)$_4$ (141 mg, 0.122 mmol) was added and the reaction mixture was heated using a microwave reactor at 100° C. for 1 h. The reaction mixture was diluted with water (50 mL) and extracted with DCM (3×50 mL). The combined organic fractions were dried (MgSO$_4$) and concentrated in vacuo. The residue was purified by column chromatography, dissolved in DCM (10 mL) and TFA (2 mL) and stirred for 3 h. The reaction mixture was concentrated in vacuo and the residue was dissolved in 1M aq. Na$_2$CO$_3$ (25 mL) and extracted with DCM (3×25 mL). The combined organic fractions were dried (MgSO$_4$) and concentrated in vacuo. The residue was purified by column chromatography to give the title compound as a white solid (149 mg, 62.8%). HRMS (ESI$^+$) calcd for [MH]$^+$ of $C_{23}H_{21}ClN_4$ 389.1533. found 389.1537. HPLC: Rt 3.42 min, 97.5% purity.

Example 18

5-[1-(4-Chlorophenyl)-3-(piperidin-4-yl)-1H-pyrrolo[2,3-c]pyridin-2-yl]pyridin-2-amine

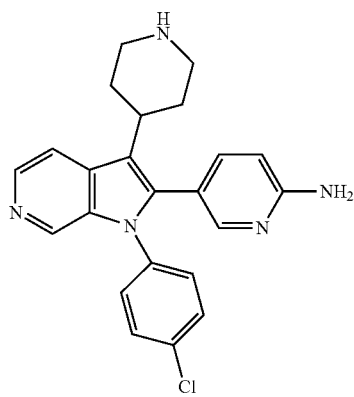 [SMILES: Nc1ccc(-c2c(C3CCNCC3)c3ccncc3n2-c2ccc(Cl)cc2)cn1]

Example 18 was prepared similarly to Example 17, using 2-amino-5-(4,4,5,5-tetramethyl-1,3,2-dioxaborolan-2-yl)pyridine instead of 4-pyridineboronic acid pinacol ester, to give the title compound as an off white solid (9.41 mg, 6.25%). HRMS (ESI$^+$) calcd for [MH]$^+$ of $C_{23}H_{22}ClN_5$ 404.1642. found 404.1647. HPLC: Rt 3.34 min, 98.5% purity.

Example 19

{[1-(4-Chlorophenyl)-2-(pyridin-4-yl)-1H-pyrrolo[2,3-c]pyridin-3-yl]methyl}dimethyl amine

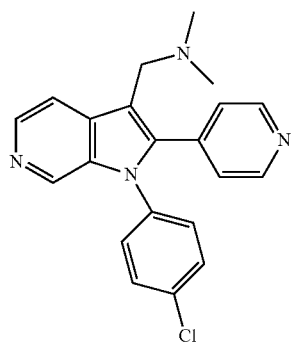 [SMILES: CN(C)Cc1c(-c2ccncc2)n(-c2ccc(Cl)cc2)c2cnccc12]

Intermediate 15 (372 mg, 1.22 mmol) was dissolved in MeCN (20 mL), N,N-dimethylmethyleneiminum iodide (1.35 g, 7.32 mmol) was added portion-wise and the reaction mixture was heated at 80° C. for 34 h. The reaction mixture was concentrated in vacuo and partitioned between DCM (50 mL) and 1M aq. $Na_2CO_3$ (50 mL) and the organic fraction was dried ($MgSO_4$) and concentrated in vacuo. The residue was purified by column chromatography and reverse phase HPLC to give the title compound as a yellow gum (115 mg, 25.9%). HRMS (ESI$^+$) calcd for [MH]$^+$ of $C_{21}H_{19}ClN_4$ 363.1376. found 363.1385. HPLC: Rt 3.42 min, 100% purity.

Example 20

{[1-(4-Chlorophenyl)-2-(pyridin-3-yl)-1H-pyrrolo[2,3-c]pyridin-3-yl]methyl}dimethyl amine

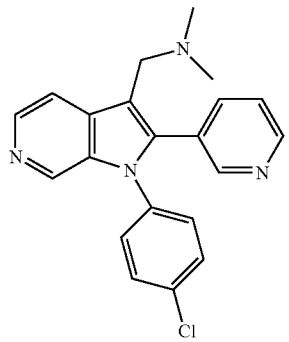 [SMILES: CN(C)Cc1c(-c2cccnc2)n(-c2ccc(Cl)cc2)c2cnccc12]

Example 20 was prepared similarly to Example 19, using Intermediate 16 instead of Intermediate 15, to give the title compound as a yellow solid (127 mg, 25.4%). HRMS (ESI$^+$) calcd for [MH]$^+$ of $C_{21}H_{19}ClN_4$ 363.1376. found 363.1376. HPLC: Rt 3.87 min, 100% purity.

Example 21

4-[1-(4-Chlorophenyl)-2-(2H-1,2,3,4-tetrazol-5-yl)-1H-pyrrolo[2,3-c]pyridin-3-yl]piperidine; bis(trifluoroacetic acid)

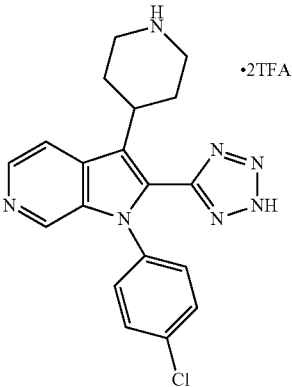 [SMILES: Clc1ccc(-n2c(-c3nn[nH]n3)c(C3CCNCC3)c3ccncc32)cc1]

Intermediate 17 (350 mg, 0.801 mmol) and $Cu_2O$ (3.44 mg, 24.0 umol) were suspended in DMF (1.4 mL) and MeOH (140 uL). Trimethylsilyl azide (232 uL, 1.76 mmol) was added and the reaction mixture stirred for 10 min and then heated in a sealed tube at 100° C. for 2 d. The reaction mixture was cooled to 0° C. and quenched with sat. aq. $NaNO_2$ (2 mL). The reaction mixture was stirred at 0° C. for 15 min and 1M aq. HCl (3 mL) was added drop-wise. The reaction mixture was stirred at 0° C. for 30 min and at RT for 1 h. The reaction mixture was filtered and the filtrate was concentrated in vacuo. The residue was purified by reverse phase HPLC, dissolved in DCM (4 mL) and TFA (1 mL) and stirred overnight. The reaction mixture was concentrated in vacuo and purified by reverse phase HPLC to give the title compound as a white solid (10.0 mg, 2.06%). HRMS (ESI$^+$)

calcd for [MH]$^+$ of $C_{19}H_{18}ClN_7$ 380.1390. found 380.1391. HPLC: Rt 3.47 min, 97.7% purity.

Biological Tests

Biological Assays of the SSAO Enzyme Inhibitors

All primary assays were performed at RT. with purified recombinantly expressed human SSAO. Enzyme was prepared essentially as described in Öhman et al. (Protein Expression and Purification 46 (2006) 321-331). In addition, secondary- and selectivity assays were performed using SSAO prepared from various tissues or purified rat recombinant SSAO. The enzyme activity was assayed with benzylamine as substrate by measuring either benzaldehyde production, using $^{14}$C-labeled substrate, or by utilizing the production of hydrogen peroxide in a horseradish peroxidase (HRP) coupled reaction. Briefly, test compounds were dissolved in dimethyl sulfoxide (DMSO) to a concentration of 10 mM. Dose-response measurements were assayed by either creating 1:10 serial dilutions in DMSO to produce a 7 point curve or by making 1:3 serial dilutions in DMSO to produce 11 point curves. The top concentrations were adjusted depending on the potency of the compounds and subsequent dilution in reaction buffer yielded a final DMSO concentration ≤2%.

Hydrogen Peroxide Detection:

In a horseradish peroxidase (HRP) coupled reaction, hydrogen peroxide oxidation of 10-acetyl-3,7-dihydroxyphenoxazine produced resorufin, which is a highly fluorescent compound (Zhout and Panchuk-Voloshina. Analytical Biochemistry 253 (1997) 169-174; Amplex® Red Hydrogen Peroxide/peroxidase Assay kit, Invitrogen A22188). Enzyme and compounds in 50 mM sodium phosphate, pH 7.4 were set to pre-incubate in flat-bottomed microtiter plates for approximately 15 min before initiating the reaction by addition of a mixture of HRP, benzylamine and Amplex reagent. Benzylamine concentration was fixed at a concentration corresponding to the Michaelis constant, determined using standard procedures. Fluorescence intensity was then measured at several time points during 1-2 h, exciting at 544 nm and reading the emission at 590 nm. For the human SSAO assay final concentrations of the reagents in the assay wells were: SSAO enzyme 1 ug/ml, benzylamine 100 uM, Amplex reagent 20 uM, HRP 0.1 U/mL and varying concentrations of test compound. The inhibition was measured as % decrease of the signal compared to a control without inhibitor (only diluted DMSO). The background signal from a sample containing no SSAO enzyme was subtracted from all data points. Data was fitted to a four parameter logistic model and IC$_{50}$ values were calculated using the GraphPad Prism 4 or XLfit 4 programs.

Aldehyde Detection:

SSAO activity was assayed using 140-labeled benzylamine and analysed by measuring radioactive benzaldehyde. In a white 96-well optiplate (Packard), 20 uL of diluted test compound was pre-incubated at room temperature with 20 uL SSAO enzyme for approximately 15 min with continuous agitation. All dilutions were made with PBS. The reaction was initiated by adding 20 uL of the benzylamine substrate solution containing [7-140] Benzylamine hydrochloride (CFA589, GE Healthcare). The plate was incubated for 1 h as above after which the reaction was stopped by acidification (10 uL 1M aq HCl). Then 90 uL Micro Scint-E solution (Perkin-Elmer) was added to each well and the plate was continuously mixed for 15 min. Phase separation occurred instantly and activity was read in a Topcount scintillation counter (Perkin-Elmer). In the final reaction well, the human recombinant SSAO concentration was 10 ug/ml. In order to optimize sensitivity, the substrate concentration was decreased as compared to the HRP coupled assay in order to get a higher fraction of radioactive product. In the human SSAO assay, benzylamine concentration was 40 uM (0.2 uCi/mL). Data was analysed as above.

All of the exemplified compounds of the invention had an IC$_{50}$ value of between 2 nM and 340 nM at SSAO. SSAO activity data for the Examples is shown in Table 4.

hERG Assay

Compounds of the invention were tested for inhibition of the human ether a go-go related gene (hERG) K$^+$ channel using IonWorks patch clamp electrophysiology. 8 Point concentration-response curves were generated on two occasions using 3-fold serial dilutions from the maximum assay concentration (11 uM). Electrophysiological recordings were made from a Chinese Hamster Lung cell line stably expressing the full length hERG channel. Single cell ion currents were measured in the perforated patch clamp configuration (100 ug/mL amphoterocin) at room temperature using an IonWorks Quattro instrument. The internal solution contained 140 mM KCl, 1 mM MgCl$_2$, 1 mM EGTA and 20 mM HEPES and was buffered to pH 7.3. The external solution contained 138 mM NaCl, 2.7 mM KCl, 0.9 mM CaCl$_2$, 0.5 mM MgCl$_2$, 8 mM Na$_2$HPO$_4$ and 1.5 mM KH$_2$PO$_4$, and was buffered to pH 7.3. Cells were clamped at a holding potential of 70 mV for 30 s and then stepped to +40 mV for 1 s. This was followed by a hyperpolarising step of 1 s to 30 mV to evoke the hERG tail current. This sequence was repeated 5 times at a frequency of 0.25 Hz. Currents were measured from the tail step at the 5$^{th}$ pulse, and referenced to the holding current. Compounds were incubated for 6-7 min prior to a second measurement of the hERG signal using an identical pulse train. A minimum of 17 cells were required for each pIC50 curve fit. A control compound (quinidine) was used. hERG data is shown in Table 4.

TABLE 4

SSAO inhibitory activity (A: <10 nM, B: 10-100 nM, C: 100-350 nM) and hERG IC50 (D: >10 uM, E: 1-10 uM, F: 0.1 uM-1 uM)

| Compound | SSAO IC$_{50}$ (nM) | hERG IC50 |
|---|---|---|
| 1 | A | E |
| 2 | B | E |
| 3 | A | |
| 4 | A | F |
| 5 | A | |
| 6 | A | F |
| 7 | B | E |
| 8 | B | E |
| 9 | A | D |
| 10 | A | |
| 11 | A | E |
| 12 | A | D |
| 13 | B | E |
| 14 | B | D |
| 15 | C | |
| 16 | C | |
| 17 | A | E |
| 18 | B | D |
| 19 | B | E |
| 20 | C | |
| 21 | C | D |

The invention claimed is:

1. A compound of formula (I) or a pharmaceutically acceptable salt, or N-oxide thereof:

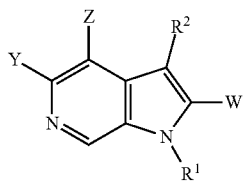
(I)

Wherein

Y is selected from hydrogen, hydroxyl, —NH$_2$, —NH—C$_{1-4}$-alkyl, —NH-halo-C$_{1-4}$-alkyl and C$_{1-4}$-alkoxy;

Z is selected from hydrogen, halogen, hydroxyl, cyano, C$_{1-4}$-alkyl, halo-C$_{1-4}$-alkyl, C$_{1-4}$-alkoxy halo-C$_{1-4}$-alkoxy, CONH$_2$, SO$_2$NH$_2$, —NH$_2$, —NH—C$_{1-4}$-alkyl, and —NH-halo-C$_{1-4}$-alkyl;

R$^1$ is a phenyl ring or a 5 or 6-membered heteroaryl ring, optionally substituted with one or more substituents selected from halogen, cyano, C$_{1-4}$-alkyl, halo-C$_{1-4}$-alkyl, cyano-C$_{1-4}$-alkyl, C$_{1-4}$-alkoxy, halo-C$_{1-4}$-alkoxy, —NR$^{4A}$R$^{4B}$, —NR$^6$C(O)OR$^5$, —NR$^6$C(O)R$^5$, NR$^6$C(O)NR$^{4A}$R$^{4B}$, —C(O)NR$^{4A}$R$^{4B}$, —C(O)R$^5$, —C(O)OR$^5$, and —NR$^6$S(O)$_2$R$^5$;

W is a phenyl ring or a 5 or 6-membered heteroaryl ring, optionally substituted with one or more substituents selected from halogen, cyano, C$_{1-4}$-alkyl, halo-C$_{1-4}$-alkyl, cyano-C$_{1-4}$-alkyl, C$_{1-4}$-alkoxy, halo-C$_{1-4}$-alkoxy, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —SO$_2$R$^5$, —SO$_2$NR$^{4A}$R$^{4B}$, and —NR$^6$S(O)$_2$R$^5$;

R$^2$ is —B-Q-[R$^3$]$_n$ or —B—R$^3$, wherein n=1, 2, 3, or 4;

B is a bond, —O—, —NR$^5$—, —C(O)—, or —C$_{1-3}$-alkylene-;

Q is a saturated or partially unsaturated 3-7 membered heterocyclic or C$_{3-7}$-cycloalkyl ring;

when R$^2$ is —B-Q-[R$^3$]$_n$, R$^3$ is selected from hydrogen, halogen, cyano, amino, hydroxyl, oxo, C$_{1-4}$-alkyl, halo-C$_{1-4}$-alkyl, C$_{1-4}$-alkoxy, C$_{1-4}$alkoxy-C$_{1-4}$alkyl, hydroxy-C$_{1-4}$-alkyl, cyano-C$_{1-4}$-alkyl, amino-C$_{1-4}$-alkyl, C$_{1-4}$-alkylamino-C$_{1-4}$-alkyl, di(C$_{1-4}$-alkyl)amino-C$_{1-4}$-alkyl, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —NR$^6$S(O)$_2$R$^5$, —S(O)$_2$R$^5$, C$_{1-4}$-alkyl-NR$^6$C(O)OR$^5$, —C$_{1-4}$-alkyl-NR$^6$C(O)NR$^{4A}$R$^{4B}$, amino-C$_{1-4}$-alkoxy-C$_{1-4}$-alkyl-, (amino-C$_{1-4}$-alkyl)-amino-C$_{1-4}$-alkyl-, —C$_{1-4}$-alkyl-C(O)R$^5$, —OC(O)R$^5$, —C$_{1-4}$-alkyl-C(O)OR$^5$, —C$_{1-4}$-alkyl-C(O)NR$^{4A}$R$^{4B}$, —C$_{1-4}$-alkyl-NR$^6$C(O)NR$^{4A}$R$^{4B}$, 3-7 membered heterocyclyl, C$_{3-7}$-cycloalkyl, 3-7 membered heterocyclyl-C$_{1-4}$-alkyl-, (3-7 membered heterocyclyl-C$_{1-4}$-alkyl)-amino-C$_{1-4}$-alkyl-, phenyl-C$_{1-4}$-alkyl, and 5 or 6-membered heteroaryl-C$_{1-4}$-alkyl, and wherein any phenyl or heteroaryl residue is optionally substituted with one or more substituents selected from halogen, cyano, C$_{1-4}$-alkyl, halo-C$_{1-4}$-alkyl, C$_{1-4}$-alkoxy, C$_{1-4}$alkoxy-C$_{1-4}$alkyl, hydroxy-C$_{1-4}$-alkyl, cyano-C$_{1-4}$-alkyl, amino-C$_{1-4}$-alkyl, C$_{1-4}$-alkylamino-C$_{1-4}$-alkyl, di(C$_{1-4}$-alkyl)amino-C$_{1-4}$-alkyl, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, and —NR$^6$S(O)$_2$R$^5$;

when R$^2$ is —B—R$^3$, R$^3$ is selected from —NH$_2$, C$_{1-4}$-alkoxy, C$_{1-4}$alkoxy-C$_{1-4}$alkyl, hydroxy-C$_{1-4}$-alkyl, cyano-C$_{1-4}$-alkyl, amino-C$_{1-4}$-alkyl, C$_{1-4}$-alkylamino-C$_{1-4}$-alkyl, di(C$_{1-4}$-alkyl)amino-C$_{1-4}$-alkyl, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A1}$R$^{4B}$, —C(O)R$^5$, —NR$^6$S(O)$_2$R$^5$, 3-7 membered heterocyclyl-C$_{1-4}$-alkyl-, phenyl-C$_{1-4}$-alkyl, and heteroaryl-C$_{1-4}$-alkyl, and wherein any phenyl or heteroaryl residue is optionally substituted with one or more substituents selected from halogen, cyano, C$_{1-4}$-alkyl, halo-C$_{1-4}$-alkyl, C$_{1-4}$-alkoxy, C$_{1-4}$alkoxy-C$_{1-4}$alkyl, hydroxy-C$_{1-4}$-alkyl, cyano-C$_{1-4}$-alkyl, amino-C$_{1-4}$-alkyl, C$_{1-4}$-alkylamino-C$_{1-4}$-alkyl, di(C$_{1-4}$-alkyl)amino-C$_{1-4}$-alkyl, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, and —NR$^6$S(O)$_2$R$^5$, provided that when R$^2$ is —B—R$^3$, and B is a bond and R$^3$ is —C(O)R$^5$, then R$^5$ is not hydrogen;

R$^{4A}$, R$^{4B}$ and R$^5$ are each independently selected from hydrogen, C$_{1-4}$-alkyl, hydroxy-C$_{1-4}$-alkyl, halo-C$_{1-4}$-alkyl, cyano-C$_{1-4}$-alkyl, amino-C$_{1-4}$-alkyl, C$_{1-4}$-alkylamino-C$_{1-4}$-alkyl, di(C$_{1-4}$-alkyl)-amino-C$_{1-4}$-alkyl, C$_{1-4}$alkoxy-C$_{1-4}$alkyl, 3-7 membered heterocyclyl-, 3-7 membered heterocyclyl-C$_{1-4}$-alkyl-, C$_{1-4}$-alkyl-NR$^6$C(O)OR$^5$, C$_{1-4}$-alkyl-NR$^6$C(O)R$^5$, (3-7 membered heterocyclyl-C$_{1-4}$-alkyl)-amino-C$_{1-4}$-alkyl-, C$_{3-7}$-cycloalkyl, and 5 or 6-membered heteroaryl-C$_{1-4}$-alkyl-, wherein the alkyl part of the 5 or 6-membered heteroaryl-C$_{1-4}$-alkyl group is optionally substituted on one or more carbon atoms with a group selected from halogen, C$_{1-4}$ alkyl, and C$_{3-7}$-cycloalkyl, or one of the carbon atoms of the same alkyl part is substituted with two C$_{1-4}$alkyl substituents which together with the carbon atom to which they are attached form a C$_{3-7}$-cycloalkyl ring, or R$^{4A}$ and R$^{4B}$ together with the nitrogen to which they are attached form a 4-7 membered cyclic amino group optionally substituted by one or more substituents selected from oxo, halogen, hydroxyl, cyano, C$_{1-4}$-alkyl, halo-C$_{1-4}$-alkyl, C$_{1-4}$-alkoxy, C$_{1-4}$ alkoxy-C$_{1-4}$alkyl, halo-C$_{1-4}$-alkoxy, —C(O)NR$^{4A}$R$^{4B}$, —CONH$_2$, —SO$_2$NH$_2$, —NH$_2$, —NHC$_{1-4}$-alkyl, —NHhalo-C$_{1-4}$-alkyl, —C(O)R$^5$, —C(O)OR$^5$, —SO$_2$R$^5$, and C$_{3-7}$-cycloalkyl;

unless otherwise specified the 3-7 membered heterocyclyl, or the heterocyclyl part of the 3-7 membered heterocyclyl-C$_{1-4}$-alkyl- or (3-7 membered heterocyclyl-C$_{1-4}$-alkyl)-amino-C$_{1-4}$-alkyl-group is optionally substituted with one or more substituents selected from C$_{1-4}$-alkyl, —C(O)OR$^5$, —C(O)R$^5$, —C(O)NR$^{4A}$R$^{4B}$, —NR$^{4A}$R$^{4B}$, —C$_{1-4}$-alkyl-C(O)NR$^{4A}$R$^{4B}$, and C$_{1-4}$alkoxy-C$_{1-4}$alkyl; and R$^{4A1}$ is selected from C$_{1-4}$-alkyl, hydroxy-C$_{1-4}$-alkyl, halo-C$_{1-4}$-alkyl, cyano-C$_{1-4}$-alkyl, amino-C$_{1-4}$-alkyl, C$_{1-4}$-alkylamino-C$_{1-4}$-alkyl, di(C$_{1-4}$-alkyl)amino-C$_{1-4}$-alkyl and C$_{1-4}$alkoxy-C$_{1-4}$alkyl; or R$^{4A1}$ and R$^{4B}$ together with the nitrogen to which they are attached form a 4-7 membered cyclic amino group optionally substituted by one or more substituents selected from oxo, halogen, hydroxyl, cyano, C$_{1-4}$-alkyl, halo-C$_{1-4}$-alkyl, C$_{1-4}$-alkoxy, C$_{1-4}$ alkoxy-C$_{1-4}$alkyl-, halo-C$_{1-4}$-alkoxy, —CONH$_2$, —SO$_2$NH$_2$, —NH$_2$, —NHC$_{1-4}$-alkyl, —NHhalo-C$_{1-4}$-alkyl, —C(O)R$^5$, —C(O)OR$^5$, —SO$_2$R$^5$, and C$_{3-7}$-cycloalkyl; and R$^6$ is hydrogen or C$_{1-4}$-alkyl.

2. A compound according to claim 1 wherein Y is H.

3. A compound according to claim 1 wherein Z is H.

4. A compound according to claim 1 wherein R$^1$ is a phenyl ring or a 6-membered heteroaryl ring, optionally substituted with one or more substituents selected from halogen, $C_{1-4}$-alkyl, and halo-$C_{1-4}$-alkyl.

5. A compound according to claim 1 wherein $R^1$ is a phenyl ring or a 6-membered heteroaryl ring, optionally substituted with one or more substituents selected from F, Cl, and $CH_3$.

6. A compound according to claim 1 wherein W is a 5 or 6-membered heteroaryl ring optionally substituted with one or more substituents selected from halogen, $C_{1-4}$-alkyl, halo-$C_{1-4}$-alkyl, $C_{1-4}$-alkoxy, halo-$C_{1-4}$-alkoxy, and —$NR^{4A}R^{4B}$.

7. A compound according to claim 1 wherein W is selected from pyridyl, pyridazinyl, pyrazinyl, pyrimidinyl, imidazolyl, pyrrolyl, tetrazolyl, oxazolyl, thiazolyl, 1,2,3-triazolyl, and 1,2,4-triazolyl, any of which is optionally substituted according to claim 1.

8. A compound according to claim 1 wherein $R^2$ is -Q-$[R^3]_n$.

9. A compound according to claim 1 wherein Q is a 7-membered saturated or partially unsaturated 7-membered heterocyclic or cycloalkyl ring.

10. A compound according to claim 1 wherein Q is a homomorpholine ring.

11. A compound according to claim 1 wherein Q is a saturated or partially unsaturated 5 or 6 membered heterocyclic or cycloalkyl ring.

12. A compound according to claim 1 wherein Q is selected from tetrahydrofuranyl, tetrahydropyranyl, pyrrolidinyl, piperidinyl, piperazinyl, morpholinyl, cyclopentyl, cyclopropyl, and cyclohexyl.

13. A compound according to claim 1 wherein $R^3$ is selected from hydrogen, $C_{1-4}$-alkyl, $C_{1-4}$-alkoxy, 3-7 membered heterocyclyl, 3-7 membered heterocyclyl-$C_{1-4}$-alkyl-, and
—C(O)$NR^{4A}R^{4B}$.

14. A compound according to claim 1 wherein Q is piperidinyl and $R^3$ is —$CONH_2$.

15. A compound according to claim 1 wherein $R^2$ is selected from the list of further $R^2$ groups as defined in the specification.

16. A compound according to claim 1 wherein $R^2$ is —B—$R^3$, B is —$C_{1-3}$-alkylene-, and —$R^3$ is —$NR^{4A}R^{4B}$.

17. A compound according to claim 16 wherein $R^{4A}$ and $R^{4B}$ are each independently selected from hydrogen and $C_{1-4}$-alkyl.

18. A compound according to claim 1 wherein W is an imidazolyl ring optionally substituted as in claim 1, and wherein the imidazolyl ring is connected to the pyrrolopyridine core via an imidazoly ring carbon atom.

19. A compound according to claim 1 selected from:
4-[2-(6-Aminopyridin-3-yl)-1-(4-chlorophenyl)-1H-pyrrolo[2,3-c]pyridin-3-yl]piperidine-1-carboxamide;
4-[1-(4-Chlorophenyl)-2-(pyrimidin-5-yl)-1H-pyrrolo[2,3-c]pyridin-3-yl]piperidine-1-carboxamide;
4-[1-(4-Chlorophenyl)-2-(6-methoxypyridin-3-yl)-1H-pyrrolo[2,3-c]pyridin-3-yl]piperidine-1-carboxamide;
4-[1-(4-Chlorophenyl)-2-(2-methoxypyridin-4-yl)-1H-pyrrolo[2,3-c]pyridin-3-yl]piperidine-1-carboxamide;
4-[1-(4-Chlorophenyl)-2-[2-(4-methylpiperazin-1-yl)pyridin-4-yl]-1H-pyrrolo[2,3-c]pyridin-3-yl]piperidine-1-carboxamide;
4-[1-(4-Chlorophenyl)-2-[6-(morpholin-4-yl)pyridin-3-yl]-1H-pyrrolo[2,3-c]pyridin-3-yl]piperidine-1-carboxamide;
4-[1-(4-Chlorophenyl)-2-(pyrimidin-5-yl)-1H-pyrrolo[2,3-c]pyridin-3-yl]piperidine-1-carboxamide;
4-[1-(4-Chlorophenyl)-2-(1H-pyrazol-3-yl)-1H-pyrrolo[2,3-c]pyridin-3-yl]piperidine-1-carboxamide;
4-[1-(4-Chlorophenyl)-2-(1H-pyrazol-4-yl)-1H-pyrrolo[2,3-c]pyridin-3-yl]piperidine-1-carboxamide;
4-[1-(4-Chlorophenyl)-2-(1-methyl-1H-pyrazol-4-yl)-1H-pyrrolo[2,3-c]pyridin-3-yl]piperidine-1-carboxamide;
4-[1-(4-Chlorophenyl)-2-(1-methyl-1H-pyrazol-5-yl)-1H-pyrrolo[2,3-c]pyridin-3-yl]piperidine-1-carboxamide;
4-[1-(4-Chlorophenyl)-2-(1-methyl-1H-imidazol-5-yl)-1H-pyrrolo[2,3-c]pyridin-3-yl]piperidine-1-carboxamide;
4-[1-(4-Chlorophenyl)-2-(1H-pyrazol-1-yl)-1H-pyrrolo[2,3-c]pyridin-3-yl]piperidine-1-carboxamide;
4-[1-(4-Chlorophenyl)-2-(1H-imidazol-1-yl)-1H-pyrrolo[2,3-c]pyridin-3-yl]piperidine-1-carboxamide;
4-[1-(4-Chlorophenyl)-2-(1H-1,2,3-triazol-1-yl)-1H-pyrrolo[2,3-c]pyridin-3-yl]piperidine-1-carboxamide;
4-[1-(4-Chlorophenyl)-2-(1H-1,2,4-triazol-1-yl)-1H-pyrrolo[2,3-c]pyridin-3-yl]piperidine-1-carboxamide;
4-[1-(4-Chlorophenyl)-3-(piperidin-4-yl)-1H-pyrrolo[2,3-c]pyridin-2-yl]pyridine;
5-[1-(4-Chlorophenyl)-3-(piperidin-4-yl)-1H-pyrrolo[2,3-c]pyridin-2-yl]pyridin-2-amine;
{[1-(4-Chlorophenyl)-2-(pyridin-4-yl)-1H-pyrrolo[2,3-c]pyridin-3-yl]methyl}dimethyl amine;
{[1-(4-Chlorophenyl)-2-(pyridin-3-yl)-1H-pyrrolo[2,3-c]pyridin-3-yl]methyl}dimethyl amine; and
4-[1-(4-Chlorophenyl)-2-(2H-1,2,3,4-tetrazol-5-yl)-1H-pyrrolo[2,3-c]pyridin-3-yl]piperidine;
and pharmaceutically acceptable salts thereof.

20. A pharmaceutical composition comprising a compound according to claim 1, and one or more suitable excipients.

* * * * *